United States Patent
Samec et al.

(10) Patent No.: US 12,182,945 B2
(45) Date of Patent: *Dec. 31, 2024

(54) MULTI-DEPTH PLANE DISPLAY SYSTEM WITH REDUCED SWITCHING BETWEEN DEPTH PLANES

(71) Applicant: Magic Leap, Inc., Plantation, FL (US)

(72) Inventors: Nicole Elizabeth Samec, Fort Lauderdale, FL (US); Nastasja U. Robaina, Coconut Grove, FL (US); Christopher M. Harrises, Nashua, NH (US); Mark Baerenrodt, Millbrae, CA (US)

(73) Assignee: MAGIC LEAP, INC., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/493,163

(22) Filed: Oct. 4, 2021

(65) Prior Publication Data

US 2022/0028175 A1    Jan. 27, 2022

Related U.S. Application Data

(63) Continuation of application No. 15/430,277, filed on Feb. 10, 2017, now Pat. No. 11,138,793.
(Continued)

(51) Int. Cl.
*G06T 19/00* (2011.01)
*G02B 27/01* (2006.01)
(Continued)

(52) U.S. Cl.
CPC ........ *G06T 19/006* (2013.01); *G02B 27/0172* (2013.01); *G06F 3/011* (2013.01);
(Continued)

(58) Field of Classification Search
None
See application file for complete search history.

(56) References Cited

U.S. PATENT DOCUMENTS

| 6,388,639 | B1 | 5/2002 | Hoshino et al. |
| 6,850,221 | B1 | 2/2005 | Tickle |
(Continued)

FOREIGN PATENT DOCUMENTS

| CN | 104641319 A | 5/2015 |
| EP | 0 849 959 | 6/1998 |
(Continued)

OTHER PUBLICATIONS

International Search Report and Written Opinion for PCT Application No. PCT/US17/17505, mailed May 8, 2017.
(Continued)

*Primary Examiner* — Michael J Hess
(74) *Attorney, Agent, or Firm* — KLINTWORTH & ROZENBLAT IP LLP

(57) ABSTRACT

Methods and systems for reductions in switching between depth planes of a multi-depth plane display system are disclosed. The display system may be an augmented reality display system configured to provide virtual content on a plurality of depth planes using different wavefront divergence. The system may monitor the fixation points based upon the gaze of each of the user's eyes, with each fixation point being a three-dimensional location in the user's field of view. Location information of virtual objects to be presented to the user are obtained, with each virtual object being associated with a depth plane. In some embodiments, the depth plane on which the virtual object is to be presented is modified based upon the fixation point of the user's eyes. For example, where the user is switching their fixation between virtual objects on two different depth planes, the display system may be configured to modify the presentation (Continued)

of one of the objects such that both objects are placed on the same depth plane.

18 Claims, 16 Drawing Sheets

Related U.S. Application Data

(60) Provisional application No. 62/445,630, filed on Jan. 12, 2017, provisional application No. 62/440,336, filed on Dec. 29, 2016, provisional application No. 62/440,332, filed on Dec. 29, 2016, provisional application No. 62/396,071, filed on Sep. 16, 2016, provisional application No. 62/366,599, filed on Jul. 25, 2016, provisional application No. 62/366,533, filed on Jul. 25, 2016, provisional application No. 62/294,147, filed on Feb. 11, 2016.

(51) Int. Cl.
*G06F 3/01* (2006.01)
*G06F 3/04842* (2022.01)
*H04N 13/122* (2018.01)
*H04N 13/128* (2018.01)
*H04N 13/332* (2018.01)
*H04N 13/383* (2018.01)
*H04N 13/395* (2018.01)

(52) U.S. Cl.
CPC .......... *G06F 3/013* (2013.01); *G06F 3/04842* (2013.01); *H04N 13/122* (2018.05); *H04N 13/128* (2018.05); *H04N 13/332* (2018.05); *H04N 13/383* (2018.05); *H04N 13/395* (2018.05); *G02B 2027/0112* (2013.01); *G02B 2027/0138* (2013.01); *G02B 2027/014* (2013.01); *G02B 2027/0178* (2013.01); *G02B 2027/0181* (2013.01); *G02B 2027/0185* (2013.01); *G02B 2027/0187* (2013.01)

(56) References Cited

U.S. PATENT DOCUMENTS

| | | |
|---|---|---|
| D514,570 S | 2/2006 | Ohta |
| 8,743,051 B1 | 6/2014 | Moy et al. |
| 8,950,867 B2 | 2/2015 | Macnamara |
| 9,081,426 B2 | 7/2015 | Armstrong |
| 9,215,293 B2 | 12/2015 | Miller |
| D752,529 S | 3/2016 | Loretan et al. |
| 9,310,559 B2 | 4/2016 | Macnamara |
| 9,348,143 B2 | 5/2016 | Gao et al. |
| D758,367 S | 6/2016 | Natsume |
| D759,657 S | 7/2016 | Kujawski et al. |
| 9,417,452 B2 | 8/2016 | Schowengerdt et al. |
| 9,470,906 B2 | 10/2016 | Kaji et al. |
| 9,489,044 B2 | 11/2016 | Fateh |
| 9,547,174 B2 | 1/2017 | Gao et al. |
| 9,671,566 B2 | 6/2017 | Abovitz et al. |
| 9,740,006 B2 | 8/2017 | Gao |
| 9,791,700 B2 | 10/2017 | Schowengerdt et al. |
| 9,851,563 B2 | 12/2017 | Gao et al. |
| 9,857,591 B2 | 1/2018 | Welch et al. |
| 9,874,749 B2 | 1/2018 | Bradski |
| 11,138,793 B2 | 10/2021 | Samec et al. |
| 2006/0028436 A1 | 2/2006 | Armstrong |
| 2007/0081123 A1 | 4/2007 | Lewis |
| 2010/0045783 A1 | 2/2010 | State et al. |
| 2011/0075257 A1 | 3/2011 | Hua et al. |
| 2012/0127062 A1 | 5/2012 | Bar-Zeev et al. |
| 2012/0162549 A1 | 6/2012 | Gao et al. |
| 2012/0218301 A1 | 8/2012 | Miller |
| 2013/0082922 A1 | 4/2013 | Miller |
| 2013/0117377 A1 | 5/2013 | Miller |
| 2013/0125027 A1 | 5/2013 | Abovitz |
| 2013/0208234 A1 | 8/2013 | Lewis |
| 2013/0215504 A1* | 8/2013 | Kim ................ H04N 13/128 359/464 |
| 2013/0229482 A1 | 9/2013 | Vilcovsky et al. |
| 2013/0242262 A1 | 9/2013 | Lewis |
| 2013/0278631 A1 | 10/2013 | Border et al. |
| 2013/0314793 A1* | 11/2013 | Robbins ............ G02B 27/0172 359/630 |
| 2014/0071539 A1 | 3/2014 | Gao |
| 2014/0078175 A1 | 3/2014 | Forutanpour et al. |
| 2014/0092006 A1 | 4/2014 | Boelter et al. |
| 2014/0177023 A1 | 6/2014 | Gao et al. |
| 2014/0218468 A1 | 8/2014 | Gao et al. |
| 2014/0267420 A1 | 9/2014 | Schowengerdt |
| 2014/0306866 A1 | 10/2014 | Miller et al. |
| 2015/0002507 A1 | 1/2015 | Ambrus et al. |
| 2015/0016777 A1 | 1/2015 | Abovitz et al. |
| 2015/0097772 A1 | 4/2015 | Stamer |
| 2015/0099252 A1 | 4/2015 | Anderson et al. |
| 2015/0103306 A1 | 4/2015 | Kaji et al. |
| 2015/0123820 A1 | 5/2015 | Merle et al. |
| 2015/0123991 A1 | 5/2015 | Yarosh et al. |
| 2015/0178939 A1 | 6/2015 | Bradski et al. |
| 2015/0205126 A1 | 7/2015 | Schowengerdt |
| 2015/0222883 A1 | 8/2015 | Welch |
| 2015/0222884 A1 | 8/2015 | Cheng |
| 2015/0234254 A1 | 8/2015 | Schowengerdt |
| 2015/0235435 A1 | 8/2015 | Miller et al. |
| 2015/0237336 A1 | 8/2015 | Sylvan et al. |
| 2015/0248169 A1 | 9/2015 | Abovitz et al. |
| 2015/0248170 A1 | 9/2015 | Abovitz et al. |
| 2015/0248788 A1 | 9/2015 | Abovitz et al. |
| 2015/0248793 A1 | 9/2015 | Abovitz et al. |
| 2015/0268415 A1 | 9/2015 | Schowengerdt et al. |
| 2015/0279117 A1 | 10/2015 | Schimke |
| 2015/0301599 A1 | 10/2015 | Miller |
| 2015/0302652 A1 | 10/2015 | Miller et al. |
| 2015/0309263 A2 | 10/2015 | Abovitz et al. |
| 2015/0326570 A1 | 11/2015 | Publicover et al. |
| 2015/0346490 A1 | 12/2015 | TeKolste et al. |
| 2015/0346495 A1 | 12/2015 | Welch et al. |
| 2015/0356781 A1 | 12/2015 | Miller |
| 2015/0363654 A1 | 12/2015 | Zhao et al. |
| 2016/0011419 A1 | 1/2016 | Gao |
| 2016/0026253 A1 | 1/2016 | Bradski et al. |
| 2016/0077337 A1 | 3/2016 | Raffle et al. |
| 2016/0085300 A1 | 3/2016 | Robbins et al. |
| 2016/0116979 A1* | 4/2016 | Border ................ G06F 3/013 345/156 |
| 2016/0134863 A1 | 5/2016 | Horesh |
| 2016/0139402 A1 | 5/2016 | Lapstun |
| 2016/0270656 A1 | 9/2016 | Samec et al. |
| 2017/0116459 A1 | 4/2017 | Chen et al. |
| 2017/0148215 A1 | 5/2017 | Aksoy et al. |
| 2017/0154464 A1 | 6/2017 | Lanier et al. |
| 2017/0178306 A1 | 6/2017 | Le Clerc et al. |
| 2017/0214907 A1 | 7/2017 | Lapstun |
| 2017/0237974 A1 | 8/2017 | Samec et al. |
| 2017/0276948 A1 | 9/2017 | Welch et al. |
| 2018/0039083 A1 | 2/2018 | Miller et al. |
| 2018/0232048 A1* | 8/2018 | Popovich ............ G02B 6/105 |

FOREIGN PATENT DOCUMENTS

| | | |
|---|---|---|
| JP | H08-166559 A | 6/1996 |
| JP | H10-333093 A | 12/1998 |
| JP | H10-333094 A | 12/1998 |
| JP | 11-109279 A | 4/1999 |
| JP | 2011-064760 A | 3/2011 |
| JP | 2011041872 A | 3/2011 |
| JP | 2011128220 A | 6/2011 |
| JP | 2013521576 A | 6/2013 |
| JP | 2013251813 A | 12/2013 |
| JP | 2015-005972 A | 1/2015 |
| JP | 2015204033 A | 11/2015 |
| JP | 2016166790 A | 9/2016 |
| KR | 2015-0005546 A | 1/2015 |
| WO | WO 2014/158633 | 10/2014 |

(56) References Cited

FOREIGN PATENT DOCUMENTS

| WO | WO2015066308 A1 | 5/2015 |
|---|---|---|
| WO | WO 2015/134740 | 9/2015 |
| WO | WO2015159533 A1 | 10/2015 |
| WO | WO 2015/184412 | 12/2015 |
| WO | WO 2017/139667 | 8/2017 |
| WO | WO 2017/165848 | 9/2017 |

OTHER PUBLICATIONS

International Preliminary Report on Patentability for PCT Application No. PCT/US17/17505, Issued Aug. 14, 2018.
"Basic Psychological Process—B.Sc. in Counseling Psychology Core Course", University of Calicut, School of Distance Education, (2011 Admission onwards) in 189 pages. URL: http://www.universityofcalicut.info/syl/CP1B01BasicPsychologicalProcesses.pdf.
"Big Tree Measuring Methods", Nature Nova Scotia, accessed Jul. 11, 2017, in 5 pages. URL: http://www.nature1st.net/naturens/files/tree_measure.html.
"Digital Mirror Fashion", GibamVision, retrieved Sep. 22, 2016, in 2 pages. URL: http://www.gibamvision.com/en/digital-mirror-fashion.
"How do I calculate total acceleration from the x, y, and z g-force values given by an accelerometer?", Quora, answered Dec. 28, 2015, accessed Jul. 11, 2017, in 4 pages. URL: https://www.quora.com/How-do-I-calculate-total-acceleration-from-the- -y-and-z-g-force-values-given-by-an-accelerometer.
"Research helps stroke victims retrain brain", Victoria University, Dec. 10, 2015, as archived Aug. 10, 2017, in 3 pages. URL: https://web.archive.org/web/20170810220140/https://www.vu.edu.au/news-events/media-releases/research-helps-stroke-victims-retrain-brain.
"Scientists Literally Stretch Brain to Map Details", Medgadget, Aug. 1, 2016, as archived Aug. 4, 2017, in 5 pages. URL: https://web.archive.org/web/20170804161858/https://www.medgadget.com/2016/08/scientists-stretch-brain.html.
"Transcranial Direct Current Stimulation Shown to Improve Learning Skills", Medgadget, Mar. 1, 2016, as archived Aug. 10, 2017, in 6 pages. URL: https://web.archive.org/save/_embed/https://www.medgadget.com/2016/03/transcranial-direct-current-stimulation-shown-improve-learning-skills.html.
"True Mirror®: See Yourself™", True Mirror, The True Mirror Company, Inc., 2015, accessed Jun. 30, 2016, in 3 pages. URL: http://www.truemirror.com/.
"True Mirrors" (homepage), True Mirror Company, as archived Aug. 17, 2017, in 2 pages. URL: https://web.archive.org/web/20170817144914/http://www.truemirror.com/.
"Eye Intensity Response, Contrast Sensitivity", Telescope-Optics.net, retrieved Jul. 11, 2017, in 14 pages. URL: http://www.telescope-optics.net/eye_intensity_response.htm.
"Eye Spectral Response", Telescope-Optics.net, retrieved Jul. 11, 2017, in 9 pages. URL: http://www.telescope-optics.net/eye_spectral_response.htm.
"Telescope images are degraded by the blurring effects of the atmosphere and by light pollution" Chapter 6-3 https://web.archive.org/web/20160726162320/http://www.public.asu.edu/~atpcs/atpcs/Univ10e/chapter06-03.html as archived Jul. 26, 2016 in 2 pages.
"The Telescopic Eye", Telescope-Optics.net, archived Jul. 21, 2016, in 5 pages. URL: https://web.archive.org/web/20160721003510/https://www.telescope-optics.net/eye.htm.
American Academy of Neurology (AAN), "Ultrasound headset may be new way to recognize concussion on the sidelines." ScienceDaily, Apr. 13, 2016, as archived Aug. 10, 2017, in 3 pages. URL: https://web.archive.org/web/20170810201930/https://www.sciencedaily.com/releases/2016/04/160413183041.htm.
Anthony, S., "MIT releases open-source software that reveals invisible motion and detail in video", Extreme Tech, Feb. 28, 2013, as accessed Aug. 4, 2017, in 5 pages.

ARToolKit: https://web.archive.org/web/20051013062315/http://www.hitl.washington.edu:80/artoolkit/documentation/hardware.htm, archived Oct. 13, 2005.
Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.
Azuma, "Predictive Tracking for Augmented Realty," TR95-007, Department of Computer Science, UNC—Chapel Hill, NC, Feb. 1995.
Banks, et al., "Insight into Vergence-Accommodation Mismatch," Proc. SPIE, May 16, 2013.
Bimber, et al., "Spatial Augmented Reality—Merging Real and Virtual Worlds," 2005 https://web.media.mit.edu/~raskar/book/BimberRaskarAugmentedRealityBook.pdf.
Binocular Visual Field, URL: https://www.med.kindai.ac.jp/optho/english/olaboratory.html Jun. 2016 in 1 page.
Brunelli, Roberto, Template Matching Techniques in Computer Vision, Theory and Practice, pp. 25-28, published 2009.
Butler, D. et al., "Mirror, Mirror, on the Wall, How Does My Brain Recognize My Image at All?" PLoS One, vol. 7, Issue 2, 2012, published online Feb. 16, 2012, in 11 pages. URL: http://www.ncbi.nlm.nih.gov/pmc/articles/PMC3281068.
Carter, T. et al., "UltraHaptics: Multi-Point Mid-Air Haptic Feedback for Touch Surfaces", UIST '13 Proceedings of the 26th Annual ACM Symposium on User Interface Software and Technology, Oct. 2013, in 10 pages. URL: http://big.cs.bris.ac.uk/wp-content/uploads/2013/10/Ultrahaptics.Carter.2013.pdf.
CNRS, "Learning to read: Tricking the brain," ScienceDaily, Aug. 28, 2014, in 3 pages. URL: http://www.sciencedaily.com/releases/2014/08/140828115248.htm.
Cornish et al., "Distribution of short-wavelength-sensitive cones in human fetal and postnatal retina: early development of spatial order and density profiles" Science Direct, Vision Research 44, 2004, in 8 pages.
Curawave: "About The Curawave (MRgFUS) Treatment", Curawave, as archived Aug. 16, 2017, in 4 pages. URL: https://web.archive.org/web/20170816232429/http://usa.uterine-fibroids.org/about-mrgfus/.
Economic and Social Research Council, "How can we still read words when the letters are jumbled up?" ScienceDaily, Mar. 15, 2013, in 2 pages. URL: https://www.sciencedaily.com/releases/2013/03/130315074613.htm.
Fotopoulou, A. et al., "Mirror-view reverses somatoparaphrenia: dissociation between first- and third-person perspectives on body ownership", Neuropsychologia, vol. 49, Dec. 2011, in 10 pages. URL: http://www.ncbi.nlm.nih.gov/pubmed/22023911.
Gilliam, C., "Can VR Justify QHD and 4K Displays?", DA Developers, Feb. 11, 2015, as archived Aug. 4, 2017, in 7 pages. URL:https://web.archive.org/web/20170804164547/https://www.da-developers.com/can-vr-justify-qhd-and-4k-displays/.
Green, M., "Night Vision", Visual E pert, as archived Aug. 4, 2017, in 9 pages. URL: https://web.archive.org/web/20170804160954/http://www.visuale pert.com/Resources/nightvision.html.
Griffith, D., "Digital neurotherapeutic' developed at UC Davis Mind Institute", Daily Democrat, Jun. 24, 2016, as archived Aug. 3, 2017, in 3 pages. URL: https://web.archive.org/web/20170803232850/http://www.dailydemocrat.com/general-news/20160624/digital-neurotherapeutic-developed-at-uc-davis-mind-institute.
Harrison, W., "Eye movement targets are released from visual crowding", Will J Harrison, Mar. 13, 2013, as archived Aug. 4, 2017, in 3 pages. URL: https://web.archive.org/web/20170804165524/http://willjharrison.com/2013/03/eye-movement-targets-are-released-from-visual-crowding/.
Hoffman, et al., "Vergence-accomodation conflicts hinder visual performance and cause visual fatigue," Jun. 1, 2010. J. Vis.; 84(3): 33.1-3330.
Hua et al., "Augmented Reality: Easy on the Eyes," Optics and Photonics News, Feb. 2015.
Hunter: Vergence-accommodation conflict is a bitch—here's how to design around it, Nov. 8, 2015.

(56) References Cited

OTHER PUBLICATIONS

HyperPhysics Concepts, Department of Physics and Astronomy, Georgia State University, https://web.archive.org/web/20170122201515/http://hyperphysics.phy-astr.gsu.edu/hbase/index.html as archived Jan. 22, 2017 in 5 pages.

HyperPhysics, "The Color-Sensitive Cones" http://hyperphysics.phyastr.gsu.edu/hbase/vision/colcon.html printed Apr. 1, 2019 in 2 pages.

Ibsen, S. et al., "Sonogenetics is a non-invasive approach to activating neurons in Caenorhabditis elegans", Nature Communications, Sep. 15, 2015, in 12 pages. URL: http://www.nature.com/ncomms/2015/150915/ncomms9264/full/ncomms9264.html.

Intel: "Retail Solution Configuration: Memory Mirror Solution", Intel, printed Sep. 25, 2015, in 3 pages. URL: http://www.intel.com/content/www/us/en/retail/nrf-2014/memory.html?wapkw=mi.

Iosa, M. et al., "Seven Capital Devices for the Future of Stroke Rehabilitation", Stroke Research and Treatment, vol. 2012, Nov. 2012, in 9 pages. URL: http://www.ncbi.nlm.nih.gov/pmc/articles/PMC3530851/.

Jacob, "Eye Tracking In Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Jurcina, K., "clinApp—Prism Adaptation", YouTube, published Dec. 7, 2015, as archived Sep. 8, 2017, in 10 pages (with video transcription). URL: https://web.archive.org/web/20170908195617/https://www.youtube.com/watch?v=k1K5qV678wQ.

Khan Academy: "The effects of ultrasound on different tissue types", Khan Academy, as archived Aug. 11, 2017, in 9 pages. URL: https://web.archive.org/web/20170811162328/https://www.khanacademy.org/test-prep/mcat/physical-sciences-practice/physical-sciences-practice-tut/e/the-effects-of-ultrasound-on-different-tissue-types.

Kolb, H., "Part XIII: Facts and Figures concerning the human retina by Helga Kolb", Webvision, archived Jul. 2, 2016, in 5 pages. URL: https://web.archive.org/web/20160702134518/http://webvision.med.utah.edu/book/part-xiii-facts-and-figures-concerning-the-human-retina/.

Kramida, et al.: "Resolving the Vergence-Accommodation Conflict in Head Mounted Displays," Aug. 27, 2015.

Le, et al., "Robust and Accurate Skeletal Rigging from Mesh Sequences," ACM Transactions on Graphics (TOG), vol. 33(4), pp. 84-93, Jul. 2014.

Matsumoto, J., "I was recently diagnosed with parkinsonism. What causes it, and how can I cope as it progresses?", Mayo Clinic, as archived Aug. 11, 2017, in 3 pages. URL: https://web.archive.org/web/20170811161634/http://www.mayoclinic.org/diseases-conditions/parkinsons-disease/e pert-answers/parkinsonism/faq-20058490.

Milde, C. et al., "Do Mirror Glasses Have the Same Effect on Brain Activity as a Mirror Bo ? Evidence from a Functional Magnetic Resonance Imaging Study with Healthy Subjects", PLoS One, vol. 10, Issue. 5, published online May 27, 2015, in 13 pages. URL: http://www.ncbi.nlm.nih.gov/pmc/articles/PMC4446290/.

MillenniumDroid, "True Mirror—Android Apps on Google Play", Google Play Store, retrieved Jun. 30, 2016, in 2 pages. URL: https://play.google.com/store/apps/details?id=com.blogspot.mdroid.mymirror&hl=en.

ModernNeurology, "Binocular Stereoscopic Depth Perception", YouTube, published Mar. 15, 2016, as archived Sep. 8, 2017, in 11 pages (with video transcription). URL: https://web.archive.org/web/20170906181457/https://www.youtube.com/watch?v=NarhP8PAdyc&feature=youtube&app=desktop.

Morries, L. et al., "Treatments for traumatic brain injury with emphasis on transcranial near-infrared laser phototherapy", Neuropsychiatric Disease and Treatment, vol. 11, Aug. 2015, in 17 pages. URL: http://www.ncbi.nlm.nih.gov/pubmed/26347062.

Mrovlje, J. et al., "Distance measuring based on stereoscopic pictures", 9th International PhD Workshop on Systems and Control: Young Generation Viewpoint, Oct. 2008, in 6 pages. URL: http://dsc.ijs.si/files/papers/S101%20Mrovlje.pdf.

Physiological Principles for the Effective Use of Color, https://web.archive.org/web/20160730010600/https://www.siggraph.org/education/materials/HyperGraph/color/coloreff.htm as archived Jul. 30, 2016 in 4 pages.

Plataforma SINC, "Through the looking glass: Research into brain's ability to understand mirror-image words sheds light on dysle ia," ScienceDaily, Mar. 31, 2011, in 3 pages, URL: https://www.sciencedaily.com/releases/2011/03/110331080037.htm.

Podda, M. et al., "Anodal transcranial direct current stimulation boosts synaptic plasticity and memory in mice via epigenetic regulation of Bdnf e pression", Scientific Reports, Feb. 24, 2016, in 19 pages. URL: http://www.nature.com/articles/srep22180.

Preston, C. et al., "Owning the body in the mirror: The effect of visual perspective and mirror view on the full-body illusion", Scientific Reports, vol. 5, published online Dec. 17, 2015, in 13 pages. URL: http://www.ncbi.nlm.nih.gov/pmc/articles/PMC4683587/.

Pullen, L., "Brain Therapy Helps Rehabilitate Stroke Patients", Medscape, Dec. 5, 2013, in 10 pages. URL: http://www.medscape.com/viewarticle/815458.

Reddit blog: "Accommodation and vergence in 3D VR," Aug. 30, 2014, in one page.

Rubinstein, M., "Eulerian Video Magnification", YouTube, published May 23, 2012, as archived Sep. 6, 2017, in 13 pages (with video transcription). URL: https://web.archive.org/web/20170906180503/https://www.youtube.com/watch?v=ONZcjs1Pjmk&feature=youtube.

Rushton, et al., "Developing Visual Systems and Exposure to Virtual Reality and Stereo Displays: Some Concerns and Speculations About the Demands on Accommodation and Vergence," Applied Ergonomics, 30 (1999) 69-78.

Rutkin, A., "Digital mirror reveals what lies under your skin", New Scientist, Apr. 15, 2014, in 3 pages. URL: https://www.newscientist.com/article/mg22229653-800-digital-mirror-reveals-what-lies-under-your-skin/.

Searle, R., "10 Crazy Facts About Mirrors," ListVerse, Dec. 30, 2013, in 11 pages. URL: http://listverse.com/2013/12/30/10-crazy-facts-about-mirrors/.

Snowbrains.com, Illustration Blind Spot, as archived May 18, 2015 in 1 page, https://web.archive.org/web/20150518201835/https://snowbrains.com/wp-content/uploads/2013/07/illustration-blind-spot.gif.

Super-resolution 3D Microscopy of Whole Cells Opens New Window for Scientists https://web.archive.org/web/20160829070151/https://www.medgadget.com/2016/07/super-resolution-3d-microscopy-whole-cells-opens-new-window-scientists.html as archived Aug. 29, 2016 and printed Apr. 16, 2019.

Szegedy et al., "Going deeper with convolutions", arXiv:1409.4842v1, Sep. 17, 2014 in 12 pages.

Szegedy et al., "Rethinking the Inception Architecture for Computer Vision", arXiv e-print arXIV:1512.00567v3, Dec. 12, 2015 in 10 pages.

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

The New York Times, "MIT Computer Program Reveals Invisible Motion in Video | The New York Times", YouTube, published Feb. 27, 2013, as archived Sep. 8, 2017, in 10 pages (with video transcription). URL: https://web.archive.org/web/20170906180629/https://www.youtube.com/watch?feature=youtu.be&t=1m5s&v=3rWycBEHn3s&app=desktop.

Vinnikov, et al., "Gaze-Contingent Depth of Field in Realistic Scenes: The User Experience," ETRA Mar. 26-28, 2014, Safety Harbor, Florida.

Wang, W. et al., "Neural Interface Technology for Rehabilitation: E ploiting and Promoting Neuroplasticity", Physical Medicine Rehabilitation Clinics of North America, vol. 21, Feb. 2010, in 22 pages. URL: http://www.ncbi.nlm.nih.gov/pmc/articles/PMC2788507/.

(56) References Cited

OTHER PUBLICATIONS

Webvision, Graph of Rod and Cone Densities along the Horizontal Meridian, https://web.archive.org/web/20170117221526/https://webvision.med.utah.edu/imageswv/Ostergr.jpeg as archived Jan. 17, 2017 in 1 page.
Webvision, Isodensity Maps of Cone Densities (X1000) in the Human Retina, as archived Jul. 22, 2016 in 1 page, https://web.archive.org/web/20160722041212/http://webvision.med.utah.edu/imageswv/Curciopl.jpeg.
Wikipedia Blind spot (vision), archived Jun. 9, 2016, in 2 pages. URL: https://web.archive.org/web/20160609224858/https:en.wikipedia.org/wiki/Blind_spot(vision).
Wikipedia, "Angular Resolution", https://web.archive.org/web/20170130060614/https://en.wikipedia.org/wiki/Angular_resolution as archived Jan. 30, 2017 in 4 pages.
Wikipedia, "Crowding", https://web.archive.org/web/20161120032119/https://en.wikipedia.org/wiki/Crowding as archived Nov. 20, 2016 in 2 pages.
Wikipedia: "Adaptation", Wikipedia, printed Jul. 11, 2017, in 9 pages. URL: https://en.wikipedia.org/wiki/Adaptation_(eye).
Wikipedia: "Atomic Mirror", Wikipedia, printed Dec. 13, 2016, in 2 pages. URL: http/en.wikipedia.org/wiki/Atomic_mirror.
Wikipedia: "Body transfer illusion", Wikipedia, as archived Aug. 10, 2017, in 4 pages. URL: https://web.archive.org/web/20170810213201/https://en.wikipedia.org/wiki/Body_transfer_illusion.
Wikipedia: "Mirror Neuron", Wikipedia, printed Jun. 30, 2016, in 17 pages. URL: https://en.wikipedia.org/wiki/Mirror_neuron.
Wikipedia: "Non-reversing mirror," Wikipedia, printed Jun. 30, 2016, in 2 pages. URL: https://en.wikipedia.org/wiki/Non-reversing_mirror.
Wikipedia: "Parkinsonism", Wikipedia, as archived Aug. 10, 2017, in pages. URL: https://web.archive.org/web/20170810214355/https://en.wikipedia.org/wiki/Parkinsonism.
Wikipedia: "Peripheral vision", Wikipedia, as archived Aug. 3, 2017, in 6 pages. URL: https://web.archive.org/web/20170803223449/https://en.wikipedia.org/wiki/Peripheral_vision.
"Positron emission tomography", Wikipedia, as archived Aug. 3, 2017, in 14 pages. URL: https://web.archive.org/web/20170803232043/https://en.wikipedia.org/wiki/Positron_emission_tomography.
Wikipedia: "Prism adaptation", Wikipedia, as archived Aug. 10, 2017, in 5 pages. URL: https://web.archive.org/web/20170810213634/https://en.wikipedia.org/wiki/Prism_adaptation.
Wikipedia: "Super-resolution imaging", Wikipedia, printed Jul. 6, 2016, in 6 pages. URL: https://en.wikipedia.org/wiki/Super-resolution_imaging.
Zult, T. et al., "Mirror illusion reduces motor cortical inhibition in the ipsilateral primary motor corte during forceful unilateral muscle contractions", Journal of Neurophysiology, vol. 113, Issue 7, Apr. 2015, published online Jan. 28, 2015, in 14 pages. URL: http://www.ncbi.nlm.nih.gov/pmc/articles/PMC4416555/.
Telescope-optics.net, "Eye Chromatism", https://web.archive.org/web/20160310131809/http://www.telescope-optics.net/eye_chromatism.htm as archived Mar. 10, 2016 in 5 pages.
Wikipedia, "Fovea Centralis," https://web.archive.org/web/20170120175611/https://en.wikipedia.org/wiki/Fovea_centralis as archived Jan. 20, 2017 in 8 pages.
Sunnex Biotechnologies, "The Role of Blue Light in the Pathogenesis of AMD" https://web.archive.org/web/20160820011045/http://www.sunnexbiotech.com/therapist/blue%20light%20and%20amd.html as archived Aug. 20, 2016 in 20 pages.

\* cited by examiner

MULTI-DEPTH PLANE DISPLAY SYSTEM WITH REDUCED SWITCHING BETWEEN DEPTH PLANES

CROSS-REFERENCE TO RELATED APPLICATIONS

This application is a continuation of U.S. application Ser. No. 15/430,277, filed Feb. 10, 2017, entitled "MULTI-DEPTH PLANE DISPLAY SYSTEM WITH REDUCED SWITCHING BETWEEN DEPTH PLANES", which claims the benefit of priority under 35 U.S.C. § 119(e) of: U.S. Provisional Application No. 62/294,147, filed on Feb. 11, 2016, entitled "AUGMENTED REALITY SYSTEMS AND METHODS UTILIZING VIEWER REFLECTIONS"; U.S. Provisional Application No. 62/366,533, filed on Jul. 25, 2016, entitled "AUGMENTED REALITY SYSTEMS AND METHODS UTILIZING REFLECTIONS"; U.S. Provisional Application No. 62/440,336, filed on Dec. 29, 2016, entitled "AUGMENTED REALITY SYSTEMS AND METHODS UTILIZING REFLECTIONS"; U.S. Provisional Application No. 62/445,630, filed on Jan. 12, 2017, entitled "AUGMENTED REALITY SYSTEMS AND METHODS UTILIZING REFLECTIONS"; U.S. Provisional Application No. 62/366,599, filed Jul. 25, 2016, entitled "IMAGING MODIFICATION, DISPLAY AND VISUALIZATION USING AUGMENTED AND VIRTUAL REALITY EYEWEAR"; U.S. Provisional Application No. 62/396,071, filed Sep. 16, 2016, entitled "IMAGING MODIFICATION, DISPLAY AND VISUALIZATION USING AUGMENTED AND VIRTUAL REALITY EYEWEAR"; U.S. Provisional Application No. 62/440,332 filed Dec. 29, 2016, entitled "IMAGING MODIFICATION, DISPLAY AND VISUALIZATION USING AUGMENTED AND VIRTUAL REALITY EYEWEAR"; each of which is hereby incorporated by reference in its entirety for all purposes.

In addition, this application incorporates by reference the entirety of each of the following patent applications: U.S. application Ser. No. 14/555,585 filed on Nov. 27, 2014; U.S. application Ser. No. 14/690,401 filed on Apr. 18, 2015; U.S. application Ser. No. 14/212,961 filed on Mar. 14, 2014; and U.S. application Ser. No. 14/331,218 filed on Jul. 14, 2014.

BACKGROUND

Field

The present disclosure relates to display systems, including augmented reality imaging and visualization systems.

Description of the Related Art

Modern computing and display technologies have facilitated the development of systems for so called "virtual reality" or "augmented reality" experiences, in which digitally reproduced images or portions thereof are presented to a user in a manner wherein they seem to be, or may be perceived as, real. A virtual reality, or "VR", scenario typically involves the presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, an MR scenario may include AR image content that appears to be blocked by or is otherwise perceived to interact with objects in the real world.

Referring to FIG. 1, an augmented reality scene 10 is depicted. The user of an AR technology sees a real-world park-like setting 20 featuring people, trees, buildings in the background, and a concrete platform 30. The user also perceives that he/she "sees" "virtual content" such as a robot statue 40 standing upon the real-world platform 30, and a flying cartoon-like avatar character 50 which seems to be a personification of a bumble bee. These elements 50, 40 are "virtual" in that they do not exist in the real world. Because the human visual perception system is complex, it is challenging to produce AR technology that facilitates a comfortable, natural-feeling, rich presentation of virtual image elements amongst other virtual or real-world imagery elements.

Systems and methods disclosed herein address various challenges related to AR and VR technology.

SUMMARY

Some non-limiting embodiments include a system comprising one or more processors and one or more computer storage media storing instructions that, when executed by the one or more processors, cause the one or more processors to perform operations. The operations comprise determining a fixation point of a user's eyes, wherein the fixation point is a three-dimensional location in a field of view of the user; obtaining location information associated with a first virtual object to present to the user, wherein the first virtual object has an associated depth from the user; adjusting one or more depth cues of the first virtual object to reduce differences between the depth cues of the first virtual object and depth cues for the fixation point; and causing presentation to the user, via a display device, of the first virtual object with the adjusted one or more depth cues.

In some other embodiments, aa display system is provided. The display system comprises a display device configured to present virtual objects to a user, each virtual object on one or more depth planes of a plurality of depth planes; one or more processors; and one or more computer storage media storing instructions that when executed by the display system, cause the display system to perform operations. The operations comprise monitoring information associated with eye movements of the user; determining, based on the monitored information, a fixation point of the eyes of the user, each fixation point indicating a three-dimensional location being fixated upon by the eyes of the user, tracked over time; and based on the determined fixation points, adjusting at least one virtual object such that the at least one virtual object is displayed on a same depth plane as corresponds to the depth plane region that a determined fixation point falls within for greater than a threshold metric. The determined fixation point is determined to fall within the depth plane region for greater than a threshold metric before adjusting the at least one virtual object.

An embodiment of a method is described. The method is performed by a system comprising one or more processors. The method comprises determining a fixation point of a user's eyes, wherein the fixation point is a three-dimensional location in a field of view of the user; obtaining location information associated with a first virtual object to present to the user, wherein the first virtual object has an associated depth from the user; adjusting one or more depth cues of the first virtual object to reduce differences between the depth cues of the first virtual object and depth cues for the fixation point; and causing presentation to the user, via a display device, of the first virtual object with the adjusted one or more depth cues.

DETAILED DESCRIPTION

Figure 1:
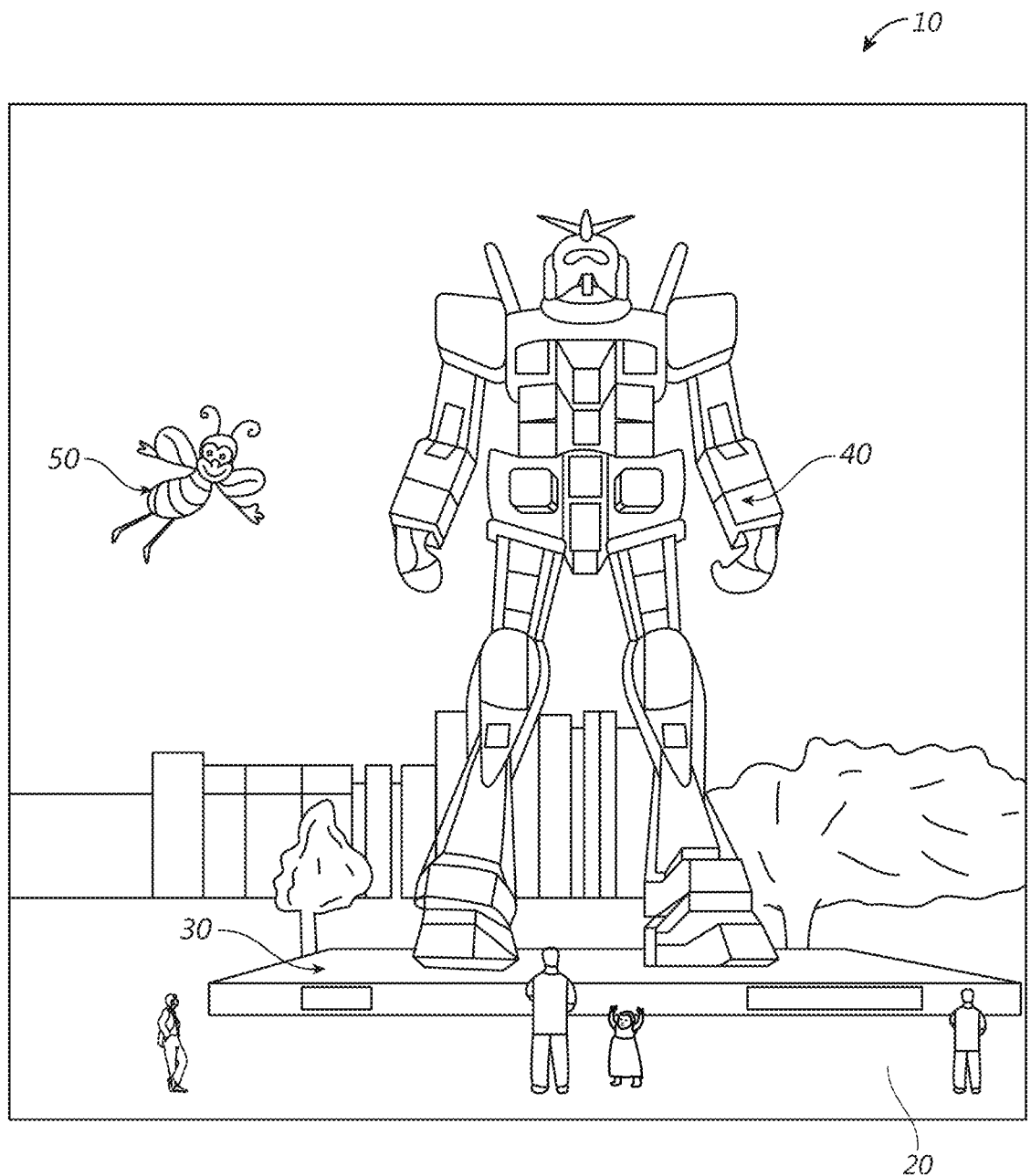
FIG. 1 illustrates a user's view of augmented reality (AR) through an AR device.

Augmented reality display systems may present virtual content to a user (or viewer), with the virtual content appearing to be located at three-dimensional locations in space in the user's field of view. The virtual content may also be referred to as virtual objects, which may include images, graphics, and other visual content that may be presented by the display system to the user. The display system may present different virtual objects at distinct depths or distances from the user, such that from the user's perspective, each virtual object may be associated with a three-dimensional location. The three-dimensional location may correspond to a position on a horizontal axis, a position on a vertical axis, and a position on the depth axis away from the user. As the user switches from viewing a near virtual object, for example, to viewing a farther virtual object, or vice versa, changes in vergence and/or accommodation may occur. As will be described in more detail below, vergence relates to the directional movement of the user's eyes, and accommodation relates to changes in the lenses and pupils of the eyes (which may serve to focus light on the retina of the eyes).

In some embodiments, techniques are provided for adjusting the presentation of virtual objects to limit an extent to which the user's visual system changes accommodation and/or changes vergence as the user views different virtual objects, or a combination of virtual objects and real objects. For example, the presentation of a virtual object may be adjusted such that the difference between one or more depth cues for the virtual object and corresponding depth cues for other virtual objects, or real objects, is reduced. For example, the one or more depth cues for the virtual object that the user may be adjusted to be similar to corresponding depth cues for the other virtual objects, or real objects, that the user is looking between. The depth cues may include accommodation cues and/or binocular cues. As will be described, adjusting accommodation cues of a virtual object may include adjusting wavefront divergence of light being output to the user by the display system, and adjusting binocular cues may include adjusting views of the virtual object that are being provided to each eye of the user (e.g., adjusting binocular disparity). Adjusting views of the virtual object includes adjusting dichoptic presentations of the virtual object. In some embodiments, a user may switch between viewing two virtual objects being presented at different depths, and comfortably view each of the virtual objects without needing to change their accommodative response for each virtual object after a switch.

Utilizing the techniques described herein, the perceived presentation quality of virtual content may be improved. For example, perceptible visual artifacts, such as flicker caused by switching content between different depth planes, may be reduced, particularly when certain augmented reality display systems are utilized, e.g., as vari-focal display systems, as described further herein. As another example, rapid switching of fixation between a virtual object and another virtual or real object may be facilitated by reducing the need for the user to change accommodation between those objects. For instance, a change in accommodation may take a perceptible amount of time as the user's eyes focus, and this perceptible amount of time may degrade the user experience, e.g., by slowing down the user's ability to absorb information as the user is repeatedly switching their attention between two objects. This slowing down may be undesirable, for example, in contexts such as games in which quick user reactions are a basis for competitive play. Examples of other contexts include fast paced environments that require multitasking and/or high levels of attention, for example, operating rooms.

Regarding vari-focal display systems, it will be appreciated that such systems may present virtual content at discrete depth planes, with all virtual content being presented at a same depth plane for each frame presented to the user (e.g., only one depth plane is active, or outputting image information, at a time). As will be described, the vari-focal display system may determine a three-dimensional fixation point at which the user is fixating, and may select a depth plane to present all virtual content based on the fixation point. As an example of determining a fixation point, the display system may monitor the orientations and/or shapes of the user's eyes and determine a three-dimensional location at which respective determined gazes of the eyes intersect. The display system may determine that the user is viewing a particular virtual object being presented at a particular three-dimensional location, and the display system may present all virtual content at a depth plane corresponding to the three-dimensional location. In this way, the display system may ensure that the particular virtual object, and optionally other virtual content, are in focus to the user. When presenting virtual content at a subsequently selected depth plane, perceptible flicker may, as an example, be introduced as the display system switches to presenting virtual content at the subsequently selected depth plane and back again to the previous depth plane. For example, as the user modifies his/her eyes to fixate on a subsequent fixation point, the display system may select the subsequent depth plane to present virtual content in a subsequently presented frame. Errors in determining the fixation point and/or a fixation point near the interface between depth planes may cause undesired and/or random switching back and forth between the depth planes. As will be described below with respect to FIG. 11, each depth plane may encompass a particular range of depths from the user, such that a depth plane may be selected according to the three-dimensional location at which the user's eyes are fixating.

To present virtual content at discrete depth planes, a display system may include one or more waveguides configured to output light with different wavefront divergence corresponding to different depth planes. Using the different wavefront divergences, different accommodation cues may be provided to the user and the display system may cause a first virtual object to appear to be located at a first depth in the user's field of view, while causing a second virtual object (using light having different wavefront divergence) to appear to be located at a second depth in the user's field of view. Additionally, the display system may present different images to each eye of the user; for example, the display system may be a binocular display that presents slightly different views of a virtual object to each eye, with each view corresponding to the view of the virtual object by each respective eye at a given depth plane. That is, the display system may provide dichoptic presentations of the virtual object to the eyes, such that depth can, in part, be represented through binocular disparity. A virtual object may therefore be perceived by the user as existing at different depths based on the output wavefront divergence and different views of the virtual object provided to each eye.

The vari-focal display system, as described above, may therefore present all virtual content using a particular wavefront divergence (corresponding to a particular depth plane) for each frame. As the user modifies his/her fixation point, light having different wavefront divergence may be selected to present other virtual content on other depth planes. It will be appreciated that a user that is switching fixation between two objects on different depth planes may cause rapid and repeated switching between depth planes, which may be perceived by the user as flicker as the different depth planes become active at different times. In addition, as noted herein, there may be a momentary lag in the viewing of content by the user as the accommodation of their eyes changes.

The techniques described herein may advantageously be utilized to reduce the occurrence of flicker and/or the lag in viewing content caused by depth plane switching and/or display system initiated changes in the user's accommodation. It will be appreciated that the display system may have access to a map or database indicating where various virtual objects may be placed in three-dimensional space. In some embodiments, the display system may determine that a user is switching between viewing a first virtual object and either (1) a second virtual object or (2) a real-world object that are located at a different depth plane (e.g., farther or closer) from the first virtual object. The display system may then cause the objects to be presented at a same depth plane. For example, the display system may cause the first virtual object and the second virtual object to be output with same, or similar, wavefront divergence (e.g., presented via a same waveguide) regardless of whether the user is fixating on the first virtual object or second virtual object. Additionally, the display system may cause the first virtual object to be output with wavefront divergence that is associated with a depth of the real-world object. In some other embodiments, the display system may determine the depth plane at which the user is fixating and modify the depth plane indicated by the display system's map before outputting the virtual content in the first instance.

In some embodiments, the display system may reduce switching in the accommodative response of a user by adjusting an output wavefront divergence, so that a virtual object is presented with the same wavefront divergence (corresponding to the same depth plane) as another virtual object or real object, while retaining (e.g., not adjusting) the views of the virtual object that are provided to each eye. Without being limited by theory, since the views of the virtual object are unmodified, the perceived location in three-dimensional space may be preserved based on binocular cues (e.g., binocular disparity). As a result, the perceived three-dimensional location may be maintained while avoiding changes in accommodation. However, and as will be described, modifying wavefront divergence of a virtual object while retaining the same views of the virtual object presented to each eye may result in negative physiological responses (e.g., headaches, eye strain, fatigue, etc.), due to a mismatch between a perceived depth associated with a modified wavefront divergence, and a perceived depth associated with binocular disparity. The perceived depth (e.g., in diopters) associated with a particular wavefront divergence and the perceived depth (e.g., in diopters) associated with binocular disparity may be determined by the display system and the mismatch between these two values may be calculated to determine the accommodation vergence mismatch. In some embodiments, the display system may perform additional actions (in addition to modifying the output wavefront divergence) if the mismatch is greater than a threshold (e.g., 0.33 diopter). As an example, the display system may adjust binocular disparity, for example, modifying views of the virtual object provided to each eye to correspond to the depth plane associated with the wavefront divergence.

Optionally, the display system may adjust binocular disparity of a virtual object, without modifying wavefront divergence of the virtual object. That is, in contrast to the display system adjusting wavefront divergence to limit a frequency with which a user accommodates to virtual objects, the display system may adjust binocular disparity such that virtual objects are perceived to be at a same, or similar, depth plane as other objects.

While vari-focal display systems were described in portions above, other display systems referred to herein as multi-focal display systems may be utilized. A multi-focal display system may simultaneously output light with wavefront divergence associated with multiple different depth planes, such that content is simultaneously displayed on multiple depth planes for each frame presented to a user. Since the multi-focal display system may present virtual objects at different depth planes in a same frame, the multi-focal display system may avoid introducing certain visual artifacts (e.g., flicker) as a user switches his/her view to different virtual objects. However, utilizing the techniques described herein, such as adjusting a depth plane at which a virtual object is to be presented, the need to change accommodation may be reduced in conformance with the description above.

It will be appreciated that the display system may be part of an augmented reality display system, or a virtual reality display system. As one example, the display system may be transmissive and may allow the user a view of the real world, while providing virtual content in the form of images, video, interactivity, and so on, to the user. As another example, the display system may block the user's view of the real world, and virtual reality images, video, interactivity, and so on, may be presented to the user.

It will also be appreciated that various embodiments described herein may advantageously be applied in various contexts. As an example, the techniques and systems disclosed herein may be applied to healthcare contexts where virtual objects may be viewed in conjunction with real objects. For example, a surgeon may be operating on a real-life patient while wearing a display system. The display system may advantageously present medical information to the surgeon, such as heart rate information. The display system may cause the medical information to be presented on a depth plane closest to the patient, such that the surgeon may avoid having to switch accommodation between the patient and the medical information as the surgeon performs his/her duties. As another example, a user may be playing a racecar driving game while wearing a display system. The display system may present virtual content, such as an interior of the user's car and an exterior of the car (e.g., a road, competitor cars). The display system may adjust particular virtual content, such as a speedometer, to be presented on a same depth plane as the exterior of the car or as a competitor's car (e.g., a field of view through a windshield of the car). In this way, the user may easily and quickly view his/her speed while avoiding having to change accommodation to the speedometer each time he/she looks at the car's dash and view the speedometer. Additionally, flicker may be eliminated as the user views the speedometer, which may otherwise negatively affect game play.

Reference will now be made to the figures.

Figure 2:
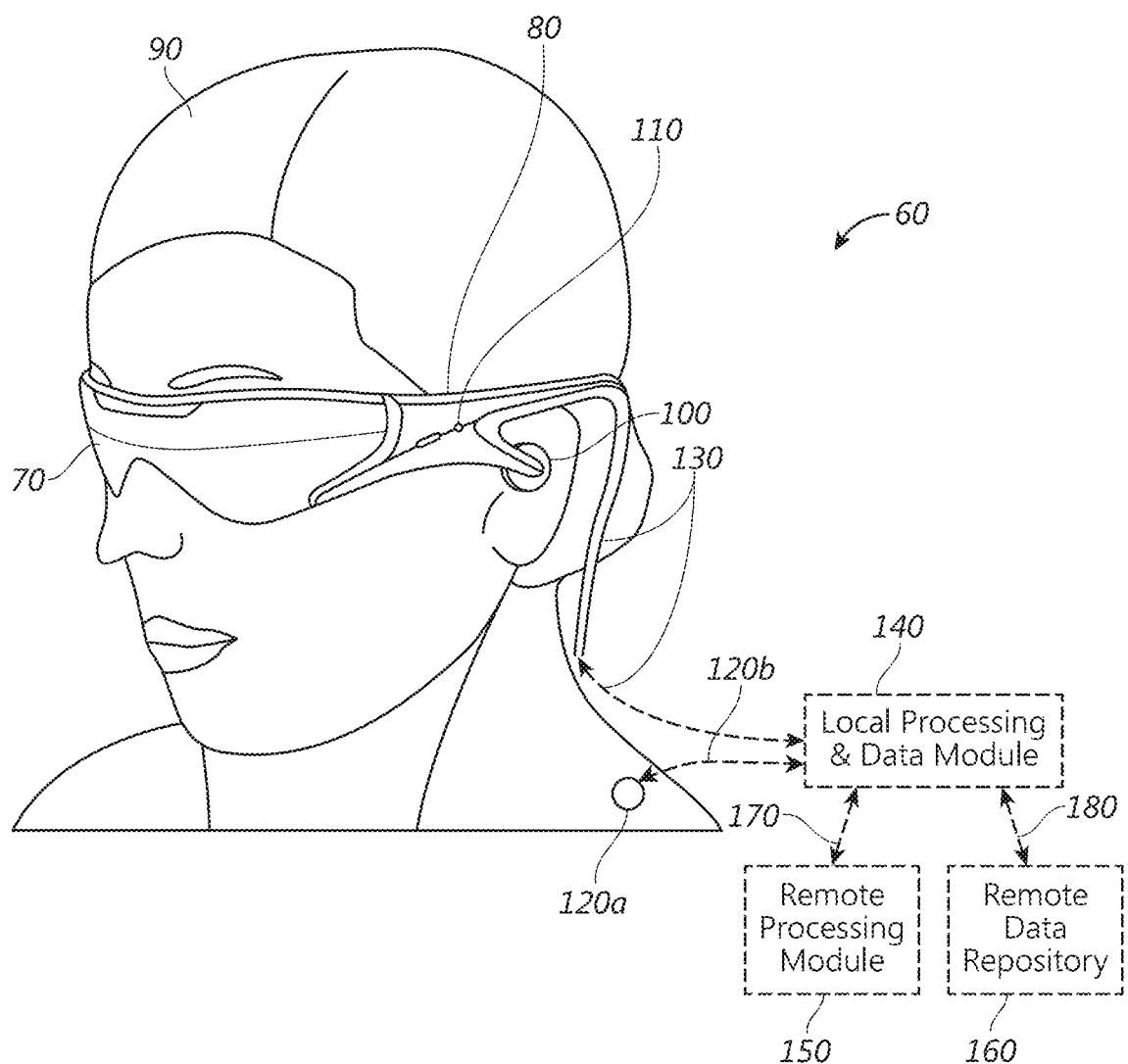
FIG. 2 illustrates an example of wearable display system.

FIG. 2 illustrates an example of wearable display system 60. The display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system may also include a peripheral sensor 120a, which may be separate from the frame 80 and attached to the body of the user 90 (e.g., on the head, torso, an extremity, etc. of the user 90). The peripheral sensor 120a may be configured to acquire data characterizing a physiological state of the user 90 in some embodiments. For example, the sensor 120a may be an electrode.

With continued reference to FIG. 2, the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120a may be operatively coupled by communications link 120b, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. Optionally, the local processor and data module 140 may include one or more central processing units (CPUs), graphics processing units (GPUs), dedicated processing hardware, and so on. The data may include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 2, in some embodiments, the remote processing module 150 may comprise one or more processors configured to analyze and process data and/or image information, for instance including one or more central processing units (CPUs), graphics processing units (GPUs), dedicated processing hardware, and so on. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating augmented reality content, to the local processing and data module 140 and/or the remote processing module 150. In some embodiments, all data is stored and all computations are performed in the local processing and data module, allowing fully autonomous use from a remote module. Optionally, an outside system (e.g., a system of one or more processors, one or more computers) that includes CPUs, GPUs, and so on, may perform at least a portion of processing (e.g., generating image information, processing data) and provide information to, and receive information from, modules 140, 150, 160, for instance via wireless or wired connections.

Figure 3:
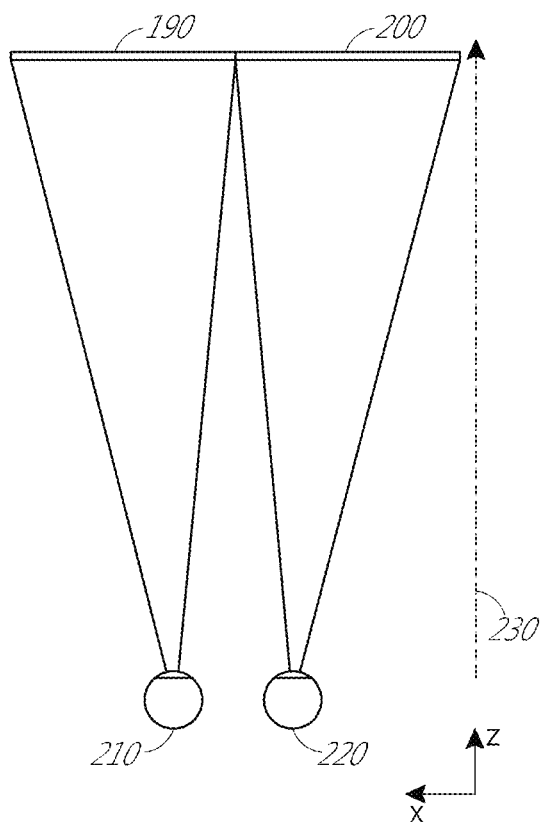
FIG. 3 illustrates a conventional display system for simulating three-dimensional imagery for a user.

With reference now to FIG. 3, the perception of an image as being "three-dimensional" or "3-D" may be achieved by providing slightly different presentations of the image to each eye of the viewer. FIG. 3 illustrates a conventional display system for simulating three-dimensional imagery for a user. Two distinct images 190, 200—one for each eye 210, 220—are outputted to the user to provide binocular cues that the user's visual system may interpret to derive a perception of depth. The images 190, 200 are spaced from the eyes 210, 220 by a distance 230 along an optical or z-axis that is parallel to the line of sight of the viewer. The images 190, 200 are flat and the eyes 210, 220 may focus on the images by assuming a single accommodated state. Such 3-D display systems rely on the human visual system to combine the images 190, 200 to provide a perception of depth and/or scale for the combined image.

It will be appreciated, however, that the human visual system is more complicated and providing a realistic perception of depth is more challenging. For example, many viewers of conventional "3-D" display systems find such systems to be uncomfortable or may not perceive a sense of depth at all. Without being limited by theory, it is believed that viewers of an object may perceive the object as being "three-dimensional" due to a combination of vergence and accommodation. Vergence movements (e.g., rotation of the eyes so that the pupils move toward or away from each other to converge the lines of sight of the eyes to fixate upon an object) of the two eyes relative to each other are closely associated with focusing (or "accommodation") of the lenses and pupils of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex," as well as pupil dilation or constriction. Likewise, a change in vergence will trigger a matching change in accommodation of lens shape and pupil size, under normal conditions. As noted herein, many stereoscopic or "3-D" display systems display a scene using slightly different presentations (and, so, slightly different images) to each eye such that a three-dimensional perspective is perceived by the human visual system. Such systems are uncomfortable for many viewers, however, since they, among other things, simply provide different presentations of a scene, but with the eyes viewing all the image information at a single accommodated state, and work against the "accommodation-vergence reflex." Display systems that provide a better match between accommodation and vergence may form more realistic and comfortable simulations of three-dimensional imagery.

Figure 4:
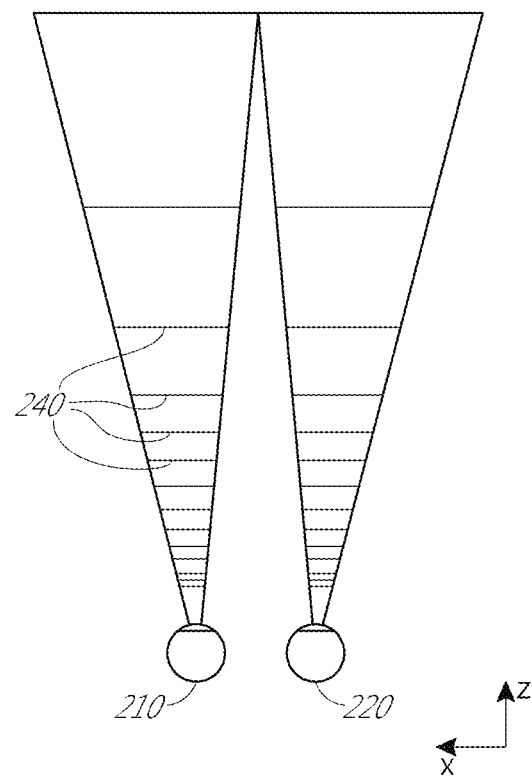
FIG. 4 illustrates aspects of an approach for simulating three-dimensional imagery using multiple depth planes.

FIG. 4 illustrates aspects of an approach for simulating three-dimensional imagery using multiple depth planes. With reference to FIG. 4, objects at various distances from eyes 210, 220 on the z-axis are accommodated by the eyes 210, 220 so that those objects are in focus. The eyes 210, 220 assume particular accommodated states to bring into focus objects at different distances along the z-axis. Consequently, a particular accommodated state may be said to be associated with a particular one of depth planes 240, which has an associated focal distance, such that objects or parts of objects in a particular depth plane are in focus when the eye is in the accommodated state for that depth plane. In some embodiments, three-dimensional imagery may be simulated by providing different presentations of an image for each of the eyes 210, 220, and also by providing different presentations of the image corresponding to each of the depth planes. While shown as being separate for clarity of illustration, it will be appreciated that the fields of view of the eyes 210, 220 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state.

Figure 5A:
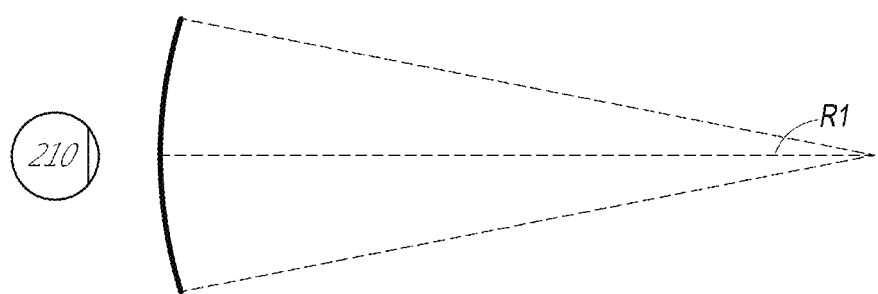
FIGS. 5A-5C illustrate relationships between radius of curvature and focal radius.
Figure 5B:
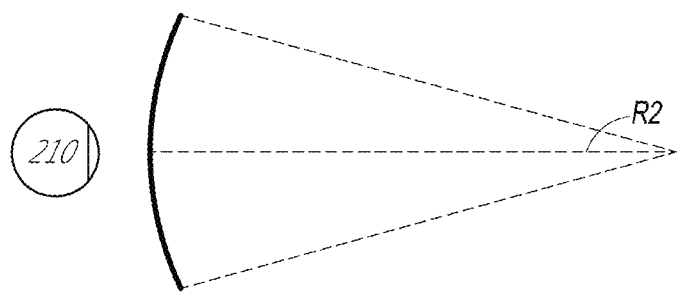
Figure 5C:
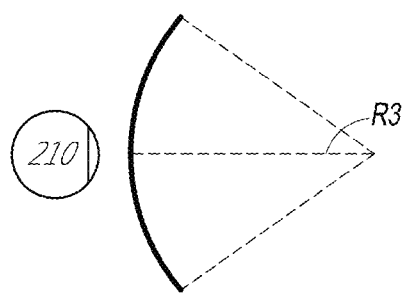

The distance between an object and the eye 210 or 220 may also change the amount of divergence of light from that object, as viewed by that eye. FIGS. 5A-5C illustrate relationships between distance and the divergence of light rays. The distance between the object and the eye 210 is represented by, in order of decreasing distance, R1, R2, and R3. As shown in FIGS. 5A-5C, the light rays become more divergent as distance to the object decreases. As distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. Consequently, at different depth planes, the degree of divergence of light rays is also different, with the degree of divergence increasing with decreasing distance between depth planes and the viewer's eye 210. While only a single eye 210 is illustrated for clarity of illustration in FIGS. 5A-5C and other figures herein, it will be appreciated that the discussions regarding eye 210 may be applied to both eyes 210 and 220 of a viewer.

Without being limited by theory, it is believed that the human eye typically can interpret a finite number of depth planes to provide depth perception. Consequently, a highly believable simulation of perceived depth may be achieved by providing, to the eye, different presentations of an image corresponding to each of these limited number of depth planes. The different presentations may be separately focused by the viewer's eyes, thereby helping to provide the user with depth cues based on the accommodation of the eye required to bring into focus different image features for the scene located on different depth plane and/or based on observing different image features on different depth planes being out of focus.

Figure 6:
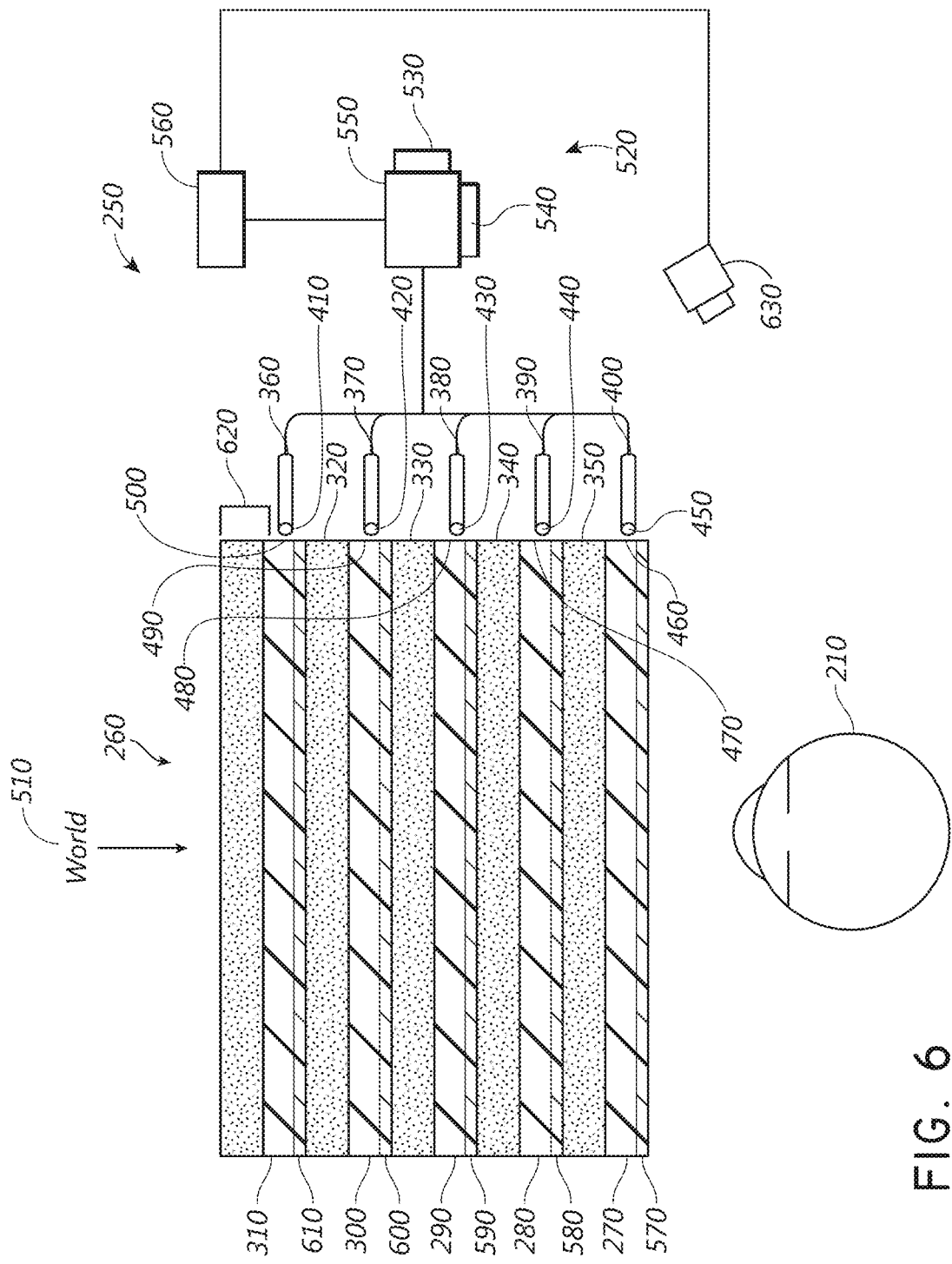
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. In some embodiments, the display system 250 is the system 60 of FIG. 2, with FIG. 6 schematically showing some parts of that system 60 in greater detail. For example, the waveguide assembly 260 may be part of the display 70 of FIG. 2. It will be appreciated that the display system 250 may be considered a light field display in some embodiments.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, the each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projector system 520, which comprises a light module 530, which may include a light emitter, such as a light emitting diode (LED). The light from the light module 530 may be directed to and modified by a light modulator 540, e.g., a spatial light modulator, via a beam splitter 550. The light modulator 540 may be configured to change the perceived intensity of the light injected into the waveguides 270, 280, 290, 300, 310. Examples of spatial light modulators include liquid crystal displays (LCD) including a liquid crystal on silicon (LCOS) displays.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 530 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 530, and the light modulator 540. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 2) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it can reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This may provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame 80 (FIG. 2) and may be in electrical communication with the processing modules 140 and/or 150, which may process image information from the camera assembly 630. In some embodiments, one camera assembly 630 may be utilized for each eye, to separately monitor each eye.

In some embodiments, an inward facing camera may also be configured to detect the accommodative response, or accommodation state, of the user's eyes, to display content to the user without requiring the user to change that accommodative response. Optionally, the inward facing camera may be configured to detect the accommodative response, or accommodation state, of each of the user's eyes. The displayed content may include alerts, menu items, or other content that may be beneficial for the user to clearly see irrespective of the depth at which their eyes are focused. In some embodiments, the display system 80 may be configured to detect shape change of the lens in the user's eyes to determine what the user's eyes are focused on and, in turn, the display system 80 may render displayed images on the appropriate depth plane with corresponding and appropriate depth cues (e.g., with appropriate resolution, detail, color saturation, contrast, etc. for particular depth planes).

Figure 7:
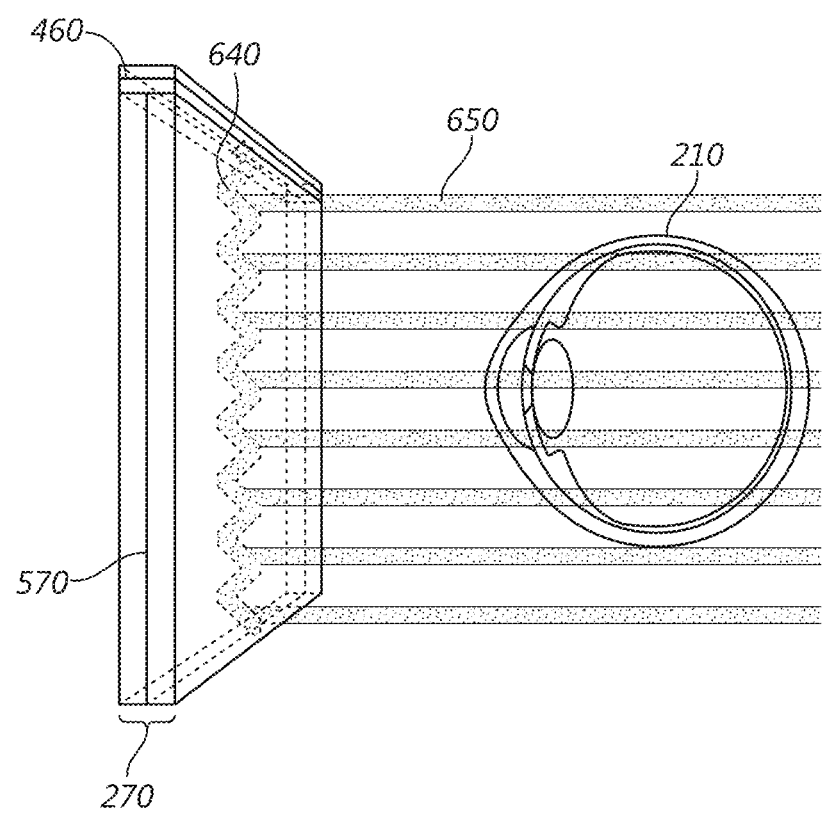
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

Figure 8:
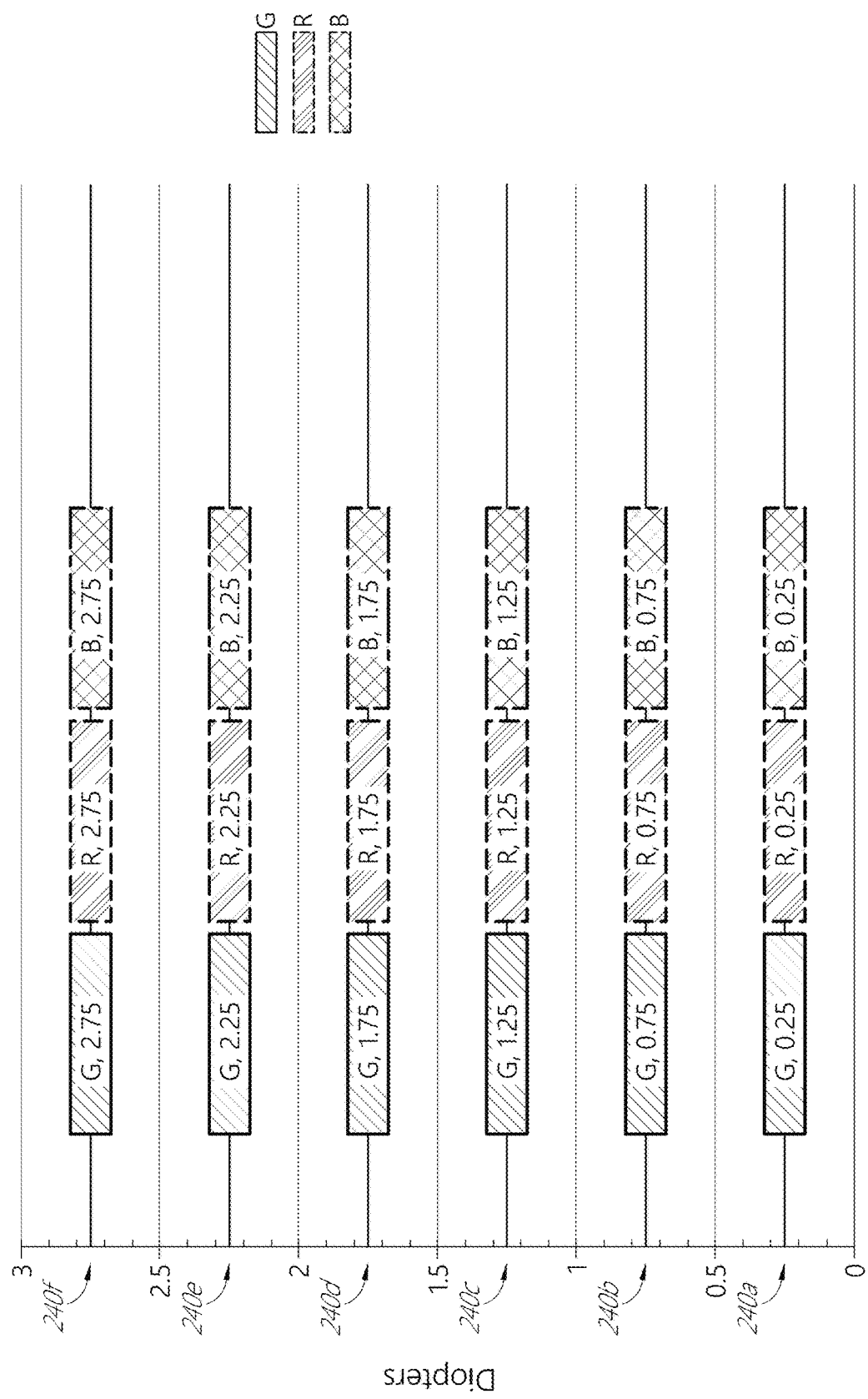
FIG. 8 illustrates an example of a stacked waveguide assembly in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 530 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
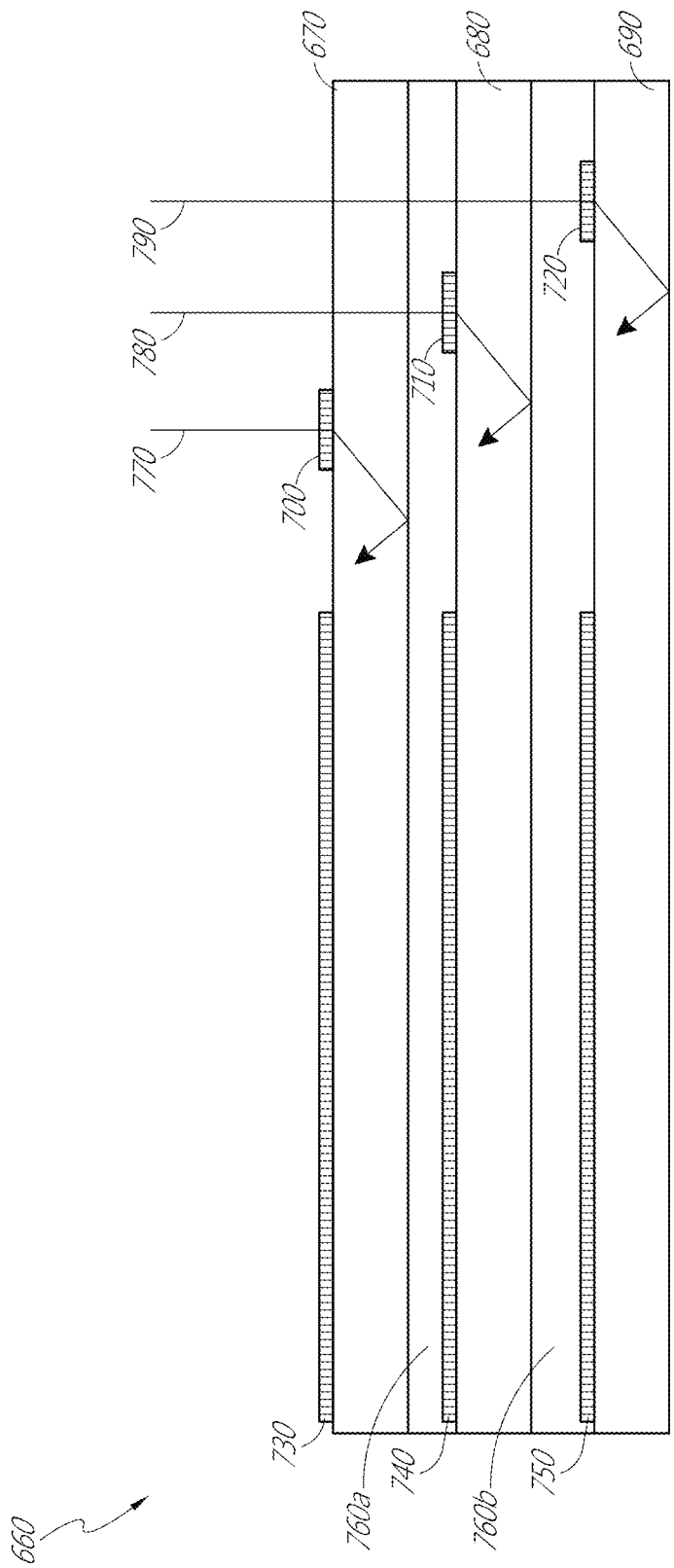
FIG. 9A illustrates a cross-sectional side view of an example of a set of stacked waveguides that each includes an incoupling optical element.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material. For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760a, 760b is 0.05 or more, or 0.10 or less than the refractive index of the material forming the waveguides 670, 680, 690. Advantageously, the lower refractive index layers 760a, 760b may function as cladding layers that facilitate total internal reflection (TIR) of light through the waveguides 670, 680, 690 (e.g., TIR between the top and bottom major surfaces of each waveguide). In some embodiments, the layers 760a, 760b are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760a, 760b are similar or the same. In some embodiments, the material forming the waveguides 670, 680, 690 may be different between one or more waveguides, and/or the material forming the layers 760a, 760b may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TIR. In some embodiments, the incoupling optical elements 700, 710, 720 each selectively deflect one or more particular wavelengths of light, while transmitting other wavelengths to an underlying waveguide and associated incoupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by TIR until impinging on the waveguide's corresponding light distributing elements 730, 740, 750.

Figure 9B:
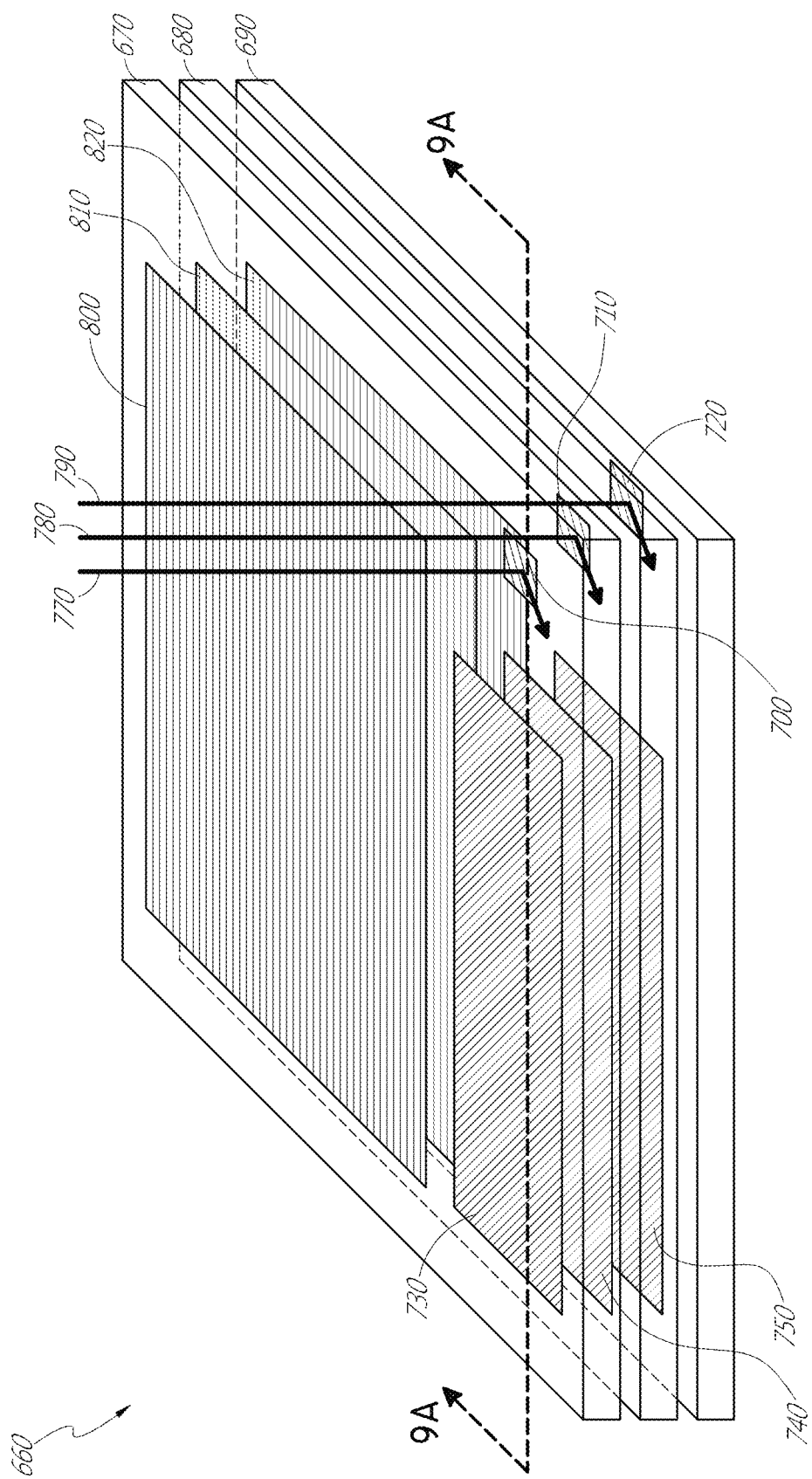
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of incoupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810. Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
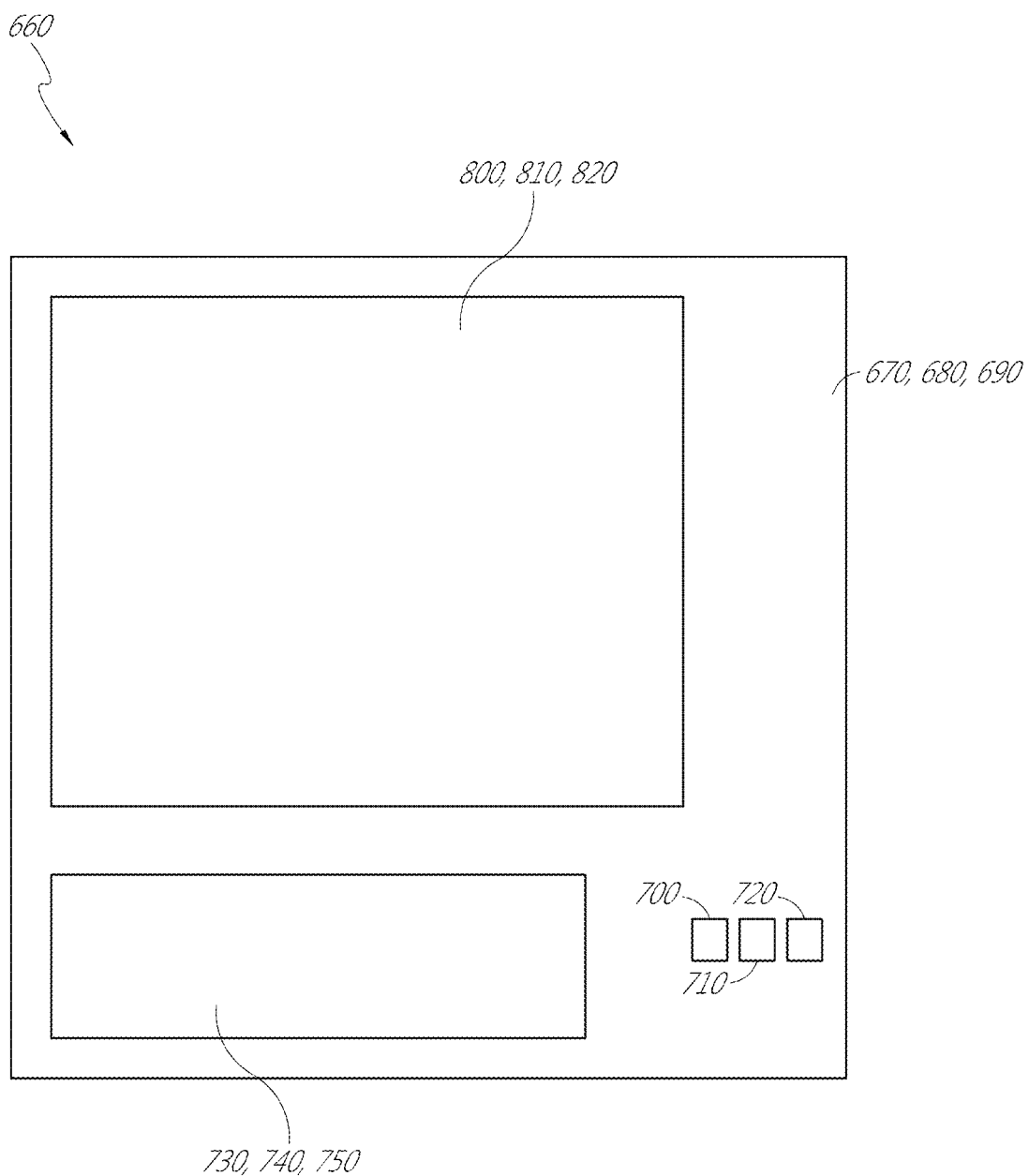
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub pupils.

As described herein, display systems (e.g., augmented reality display systems such as the display system 80, FIG. 2) according to various embodiments may adjust a depth at which a virtual object is to be presented. As described above, a virtual object that is to be presented at a first depth may be adjusted to correspond to a second depth at which a second virtual object is to be presented or at which a real object is present. It will be appreciated that the different depth may correspond to different depth planes that the display system is configured to place virtual objects on. In some embodiments, a user of the display system may therefore switch between viewing the first virtual object and the second virtual or real object without needing to change accommodation and/or without perceiving that the two objects are on different depth planes. Adjusting a depth may include adjusting one or both of accommodation cues (e.g., adjusting wavefront divergence) and binocular cues (e.g., adjusting respective views of a virtual object being provided to each eye of the user).

A display system may determine that the user is switching focus between a virtual object and a real object based on determining three-dimensional fixation points of the user. For example, the display system may determine that the user is switching fixation between virtual objects that are being presented at the determined fixation points. The fixation point may indicate the location of a point in space along (1) an x-axis (e.g., a lateral axis), (2) a y-axis (e.g., a vertical axis), and (3) a z-axis (e.g., a depth of the point, for example a depth from the user). In some embodiments, the display system may utilize sensors such as cameras (e.g. sensor 630 of FIG. 6) to monitor the user's eyes (e.g., a pupil and/or cornea, and so on, of each eye), to determine a gaze of each eye. The gaze of each eye may be understood to be a vector extending from the fovea through the lens of the eye. The display system may be configured to extrapolate where the vectors associated with the eyes intersect, and this intersection point may be understood to be the fixation point of the eyes. Stated another way, the fixation point may be a location in three-dimensional space on which the user's eyes are verging. In some embodiments, the display system may filter small movements of the user's eyes for example during rapid movements (e.g., saccades, microsaccades), and may update the fixation point upon determining that the eyes are fixating on a location in three-dimensional space. For example, the display system may be configured to ignore movements of the eye that fixate on a point for less than a threshold duration and/or ignore involuntary eye movements (e.g., blinks).

Figure 10A:
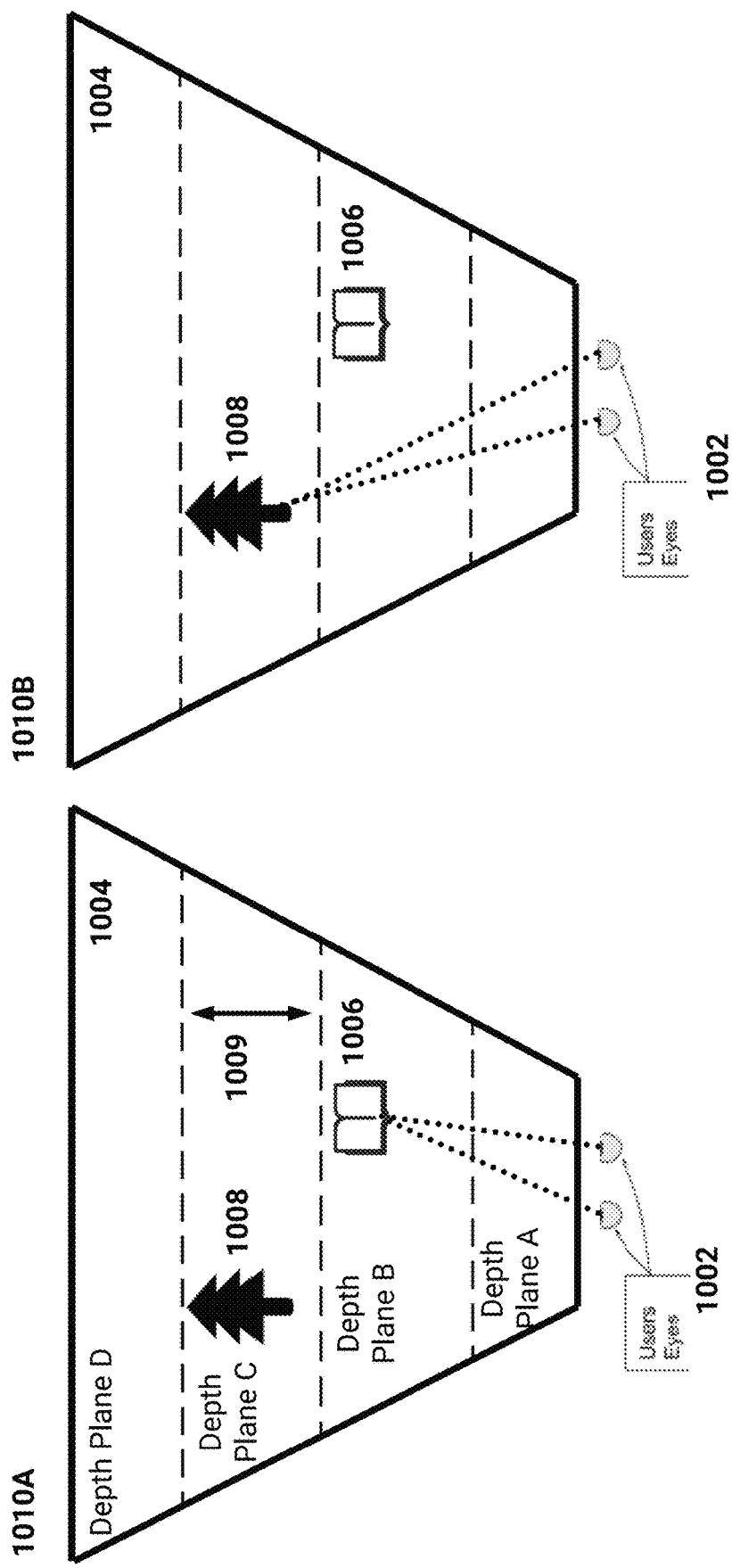
FIG. 10A illustrates an example of a representation of a user viewing content presented by a display system.

With reference now to FIG. 10A, an example is illustrated of a representation of a user viewing content (e.g., content included in a display frustum representing the user's field of view 1004) presented by a display system (e.g., the display system 80, FIG. 2). The representation includes the user's eyes 1002, and the content includes a first virtual object 1006 (e.g., a book) and a second virtual object 1008 (e.g., a tree). As an example, the user may be reading about trees as described in the first virtual object 1006 (e.g., a book, or a representation of text, may appear to be presented to the user), and as the user reads the first virtual object 1006, different representations of trees may be presented. Additionally, the book 1006 may optionally be a real-world object (e.g., an actual book), and as the user reads the book 1006, the display system may present different trees to the user corresponding to trees described in the book 1006. The first virtual object 1006, or first real-world object, and second virtual object 1008, will hereinafter be referred to as the first object and the second object, respectively.

As illustrated, the first object 1006 and the second object 1008 may be associated with different depth planes, which may be the depth planes the display system is configured to present virtual content on. In some embodiments, the perceived depth of the second object 1008 is adjusted based on the perceived depth of the first object 1006, or vice versa. As an example, if the user is determined to be fixating on the first object 1006, the virtual content may be presented at depth plane B. Alternatively, if the user is determined to be fixating on the second object 1008, the virtual content may be presented at depth plane C. As described above, the display system (e.g., a vari-focal display system) may present all virtual content at a same depth plane for each frame being presented to the user. For example, the display system may output all virtual content via a same waveguide (e.g. one of waveguides 270, 280, 290, 300, 310, FIG. 6) for each frame. As will be described below with respect to FIG. 11, each depth plane may be associated with a range of depths from the user. The display system may therefore determine a three-dimensional fixation point of the user, and select a depth plane based on a depth associated with the fixation point. For example, a depth range 1009 is associated with depth plane C, such that for a virtual object presented at a depth included in the depth range 1009, the virtual object is presented at depth plane C when fixated on by the user. While FIG. 10A illustrates four example depth planes (e.g., depth planes A-D), other quantities of depth planes may be utilized (e.g., 2, 3, or 4 or more depth planes).

Figure 10B:
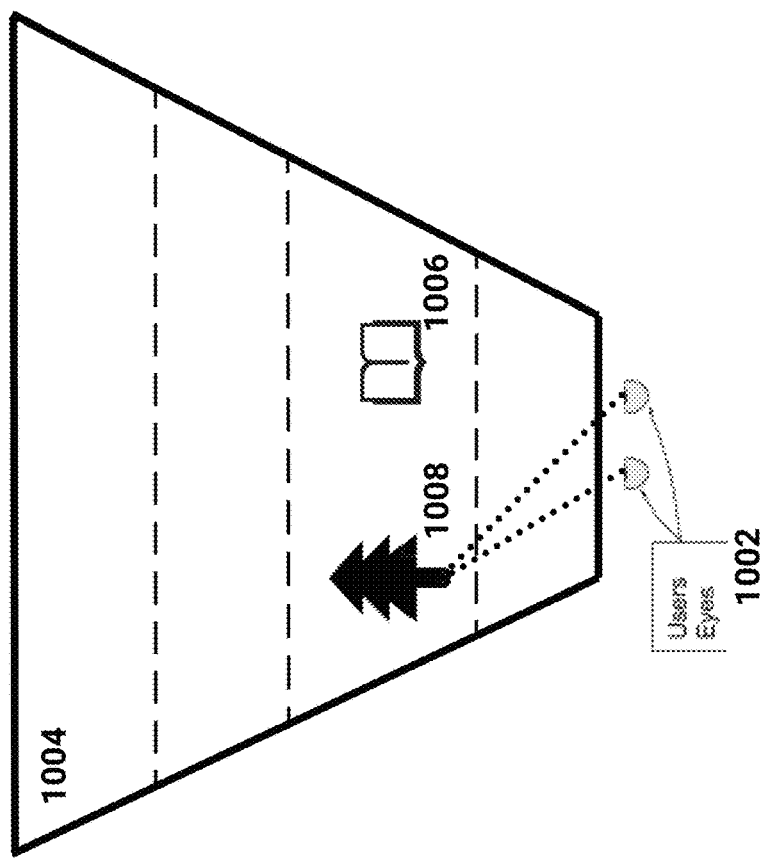
FIG. 10B illustrates another example of a representation of the user viewing content.
Figure 10B:
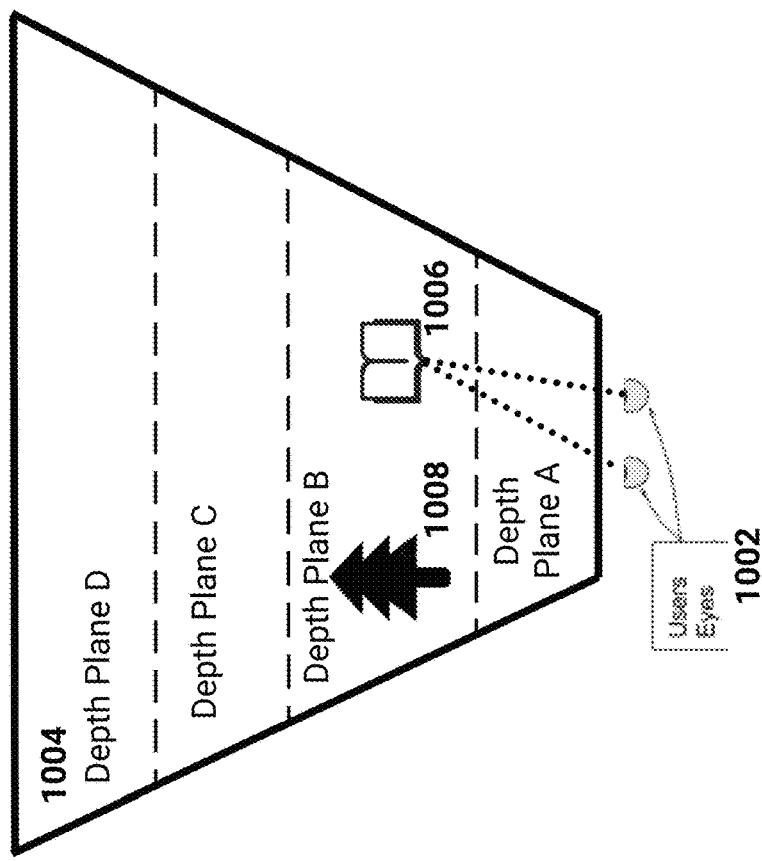

While the illustrations of FIG. 10A-10B illustrate depth planes as having planar boundaries, it will be appreciated that the sizes and shapes of the depth planes may be different than that illustrated. For example, the depth planes described herein may be curved.

With continued reference to FIG. 10A and the example scenario represented in 1010A, the user views the first object 1006. For example, the user may be fixating his/her eyes 1002 on that first object 1006. The display system may determine a fixation point of the eyes 1002, and determine that the fixation point corresponds to a location of the first object 1006. After viewing the first object 1006, the user then may fixate on the second object 1008 as shown in representation 1010B. In this example, the display system may continue to present the virtual content, e.g., the first object 1006, at a different depth plane than is associated with the second object 1008.

As described above, the first object 1006 may optionally be a real-world object. In this scenario, the display system may determine that the user is fixating on a location in three-dimensional space associated with depth plane B (e.g., corresponding to the real-world object, which may be represented by the first object 1006 in this example). The display system may present the virtual content as the second object 1008 at a depth plane associated with depth C (e.g., the second object 1008 may be presented at depth plane C).

Where both objects are virtual objects, as the user alternates fixation between the first object 1006 and the second object 1004, the display system may typically be required to change the depth planes at which the virtual content is presented, depending upon whether the first object 1006 or the second object 1008 is being fixated on. Similarly, the user's eyes 1002 are required to change accommodation as content switches between depth plane B and depth plane C. As noted herein, in some situations, switching between depth planes may undesirably cause flickering and/or momentary lags in perceiving content as the user's accommodative response adjusts to the different depth planes.

Advantageously, in some embodiments, the display system may modify a depth plane at which a virtual object is presented, and this modification may reduce the switching of the display system between depth planes and/or the switching of the accommodative response of the user's. FIG. 10B illustrates another example of a representation of the user viewing content. As illustrated, the second object 1008 has been adjusted to be associated with the same depth plane as the first object 1006. For example, the first object 1006 and the second object 1008 are both associated with or placed on depth plane B. In some embodiments, when light is output to the user to provide image information for either the first object 1006 or the second object 1008, the wavefront divergence will be the same. Therefore, the user's eyes 1002 may avoid being required to change accommodation when switching focus between the virtual objects 1006, 1008.

While a depth plane associated with the second object 1008 may be adjusted to correspond to the first object 1006, the display system may maintain (e.g., not adjust) the views (e.g., perceived depth as determined from dichoptic presentation and stereoscopic vision) of the second object 1008 that are presented to respective eyes 1002 of the user. For example, as illustrated in FIG. 10A, the second object 1008 (e.g., the tree) is positioned further in depth than the first object 1006. The second object 1008 may be adjusted such that a wavefront divergence of light representing the second object 1008 is modified (e.g., accommodation cues are adjusted). However, the second object 1008 may be perceived to still be located further in depth from the first object 1006 via binocular disparity (e.g., binocular cues may be maintained). As used herein, it will be appreciated that adjusting accommodation cues involves changing the wavefront divergence of light that provides image information for forming the user's view of a virtual object, and adjusting binocular cues involves changing the views of the virtual object presented to one or both eyes of the viewer. Adjusting accommodation cues while retaining binocular cues may result in accommodation-vergence mismatches, such that binocular disparity indicates a first depth to the user, while wavefront divergence indicates a second depth to the user. If this mismatch exceeds a threshold (e.g., 0.33 diopters or more, 0.5 diopters or more), negative physiological responses may be encountered by the user (e.g., headaches).

Optionally, the display system may determine that the mismatch exceeds the threshold, and may further adjust the binocular cues for the second object 1008 and/or the first object 1006. As an example, the views of the second object 1008 being provided to each eye of the user by the display system may be adjusted to correspond views of the second object 1008 as they would be seen at a same, or similar, depth as depth plane B (binocular cues may be adjusted). That is, the second object 1008 will be perceived as being located at a same, or similar, depth from the user as the first object 1006. While this may introduce a perceptible modification in three-dimensional location of the second object 1008, the reduction in negative physiological responses may be advantageous. Optionally, a perceived size of the second object 1008 may be adjusted according to a perceived distance that the second object 1008 appears to have moved. For example, as illustrated in FIG. 10A the second object 1008 was initially presented as being farther from the first object 1006 (e.g., based at least in part on binocular disparity). Therefore, if binocular cues are adjusted, such that the second object 1008 is perceived to be located closer to the user, the display system may scale the second virtual object 1008 so that it is perceived to be a similar size. For example, the display system may scale the second virtual object 1008 so that it takes up a same quantity (e.g., volume and/or area) of the field of view 1004 of the user. As another example, the display system may scale the second virtual object 1008 so that it matches an angular resolution of the eyes of the user. For example, the font size of text can increase for a book moved further from the user.

Optionally, the display system may determine that the mismatch exceeds the threshold, and may adjust binocular cues of the second object 1008, such that the mismatch is less than or equal to the threshold. That is, in contrast to modifying binocular cues (e.g., views of the object 1008 being provided to each eye) to correspond with a same depth as the first virtual object 1006, the display system may modify the binocular cues such that the mismatch is merely less than the threshold. This may have the effect of the second object 1008 being perceived as being closer in depth to the user, but not suddenly be perceived as being at the same depth as the first object 1006.

The display system may optionally adjust the depth of the second object 1008 upon determining that the user is switching between the first object 1006 and the second object 1008 greater than a threshold metric, e.g., greater than a threshold number of times, greater than a threshold frequency, and/or greater than a threshold duration. For example, if the user routinely fixates on the first object 1006, and rarely fixates or sporadically fixates on the second object 1008, the display system may determine not to adjust a depth plane associated with the second object 1008. On the other hand, as an example, if the user fixates back and forth between the first object 1006 and the second object 1008 over the span of several seconds, or minutes, the display system may place the first and the second object at a common depth.

That common depth may be selected based on various criteria. For example, if the first object 1006 is a real object (e.g., a book) and the second object 1008 is a virtual object, the display system may optionally adjust a depth plane associated with the second object 1008 (e.g., the adjusted depth plane may be depth plane B). In some embodiments, both the first object 1006 and the second object 1008 may be virtual objects and the determination regarding which depth plane to place both objects may be made based on which depth plane to the user is predominantly fixated on. For example, the determination may be based on an amount of time the user fixates on each virtual object. For example, if the user spends a greater quantity of time fixating on the first object 1006, the display system may adjust a depth plane associated with the second object 1008 such that the second object is placed on depth plane B. In some embodiments, the display system may obtain information indicating a preference of the user. For example, the user may indicate that he/she considers the second object 1008 to be the main virtual object, and therefore a depth plane associated with the first object 1006 may be adjusted this correspond to the depth plane of the second object 1008. Optionally, particular types of virtual objects may be identified as not being available for depth adjustment. As an example, a virtual object that contains text or fine-detail may maintain its present depth plane, while other virtual objects are adjusted.

Optionally, in addition to adjusting depth cues, the display system may adjust a location of the second virtual object 1008, e.g., such that the second virtual object 1008 is shifted in location. In some embodiments, the user may indicate a location at which the second virtual object 1008 is to be located. For example, a user that is a surgeon may prefer that virtual content in the form of medical information is displayed at a particular location with respect to a patient. The surgeon may indicate this particular location using inputs, such as hand gestures, voice input, totems, and so on. For example, the display system may recognize a hand gesture as indicating a particular location, and the display system may adjust the location of the second virtual object 1008 so that it is perceived to be at the particular location.

Figure 11:
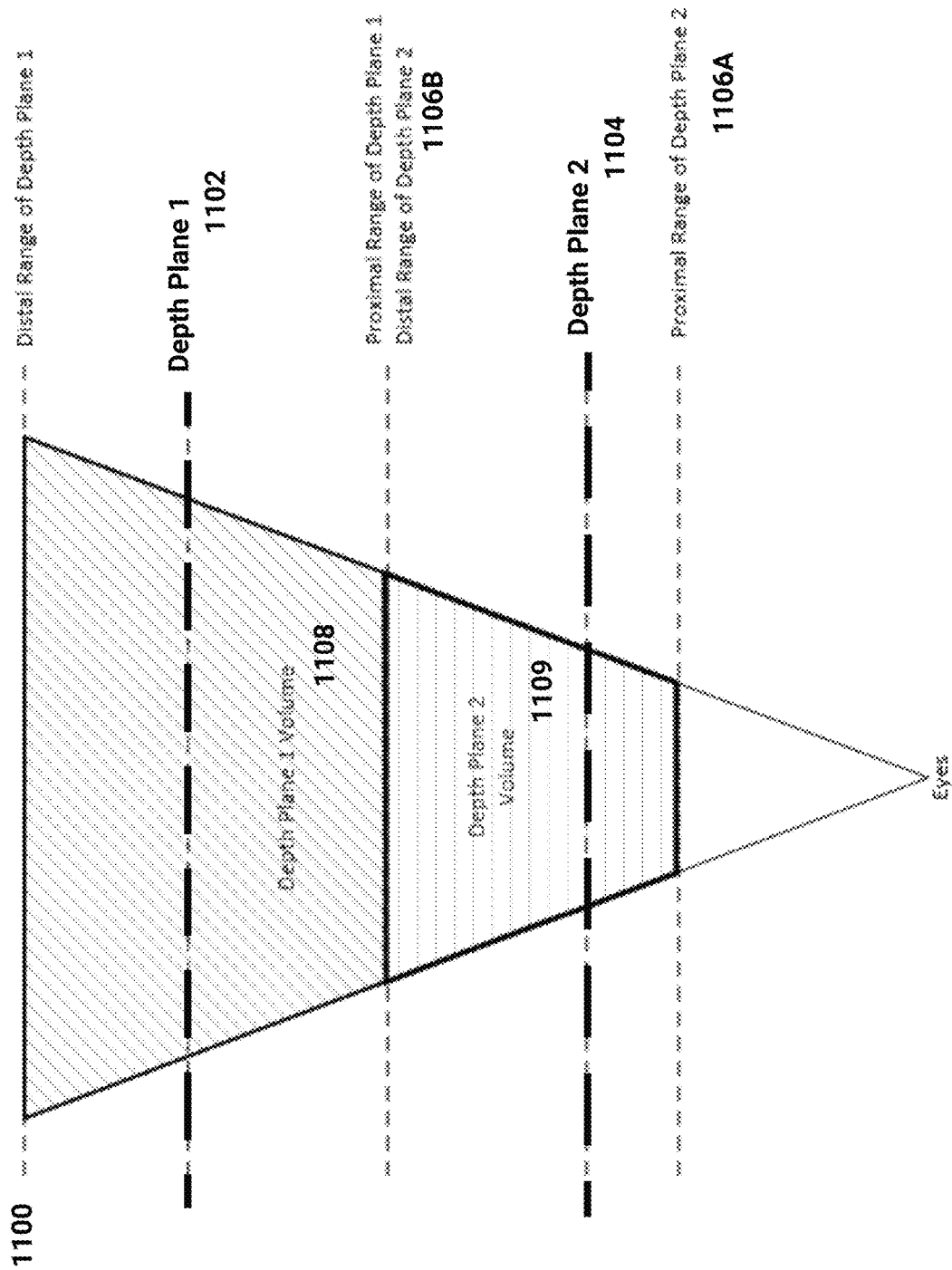
FIG. 11 illustrates a representation of a field of view of a user of a display system.

FIG. 11 illustrates a representation of a field of view 1100 of a user of a display system, to further illustrate the organization of the various depth planes. The field of view 1100 includes representations of a first depth plane 1102 and a second depth plane 1104. As illustrated, a range of depths (e.g., a volume associated with each depth plane) is illustrated as corresponding to each depth plane. For example, the proximal range of depth plane 2 extends from depth 1106A to depth 1106B. A virtual object that is to be presented at a depth within range 1106A-1106B, may be presented at depth plane 2 (also identified as reference numeral 1104). As an example, the virtual object may be output via a waveguide associated with depth plane 2. Additionally, a wavefront divergence of any virtual object to be presented at a depth within range 1106A-1106B may be the same, and therefore be associated with depth plane 2. As described above, with respect to FIG. 10A, the sizes and shapes of the depth planes can be different than as illustrated in FIG. 11. For example the volumes defining the depth planes may have curved shapes.

As described above, the display system may determine a fixation point of the user. If the fixation point falls within range 1106A-1106B, the display system may present virtual content with a wavefront divergence associated with depth plane 2. If the user then fixates on a location that falls within a range associated with depth plane 1, the display system may present content with a wavefront divergence associated with depth plane 1. As described above, the display system may be a vari-focal display system, such that for any frame being presented to the user, a single depth plane is utilized. For example, one waveguide may be utilized to output all virtual content for each frame.

In some embodiments, and as described herein, the display system may adjust depth planes at which to present particular virtual objects. In this way, the display system may limit an extent to which a depth plane selected to present virtual content needs to be modified. As an example, a first object may be presented in depth plane 1 volume 1108, and a second object may be presented in depth plane 2 volume 1109. Without utilizing the techniques described herein, as the user fixates on a first object, the display system may present the first object and the second object on depth plane 2 1104 (e.g., via a same waveguide associated with depth plane 2 1104). Subsequently, as the user switches fixation to be on the second object, the display may present the first object and the second object via depth plane 1 1102. In contrast, in some embodiments, as the user changes fixation between the first object and the second object, both objects may be placed on the same depth plane. That is, a depth plane associated with either the first object or the second object may be adjusted, so that either depth plane 2 1104 or depth plane 1 1102 may be associated with both objects.

Figure 12:
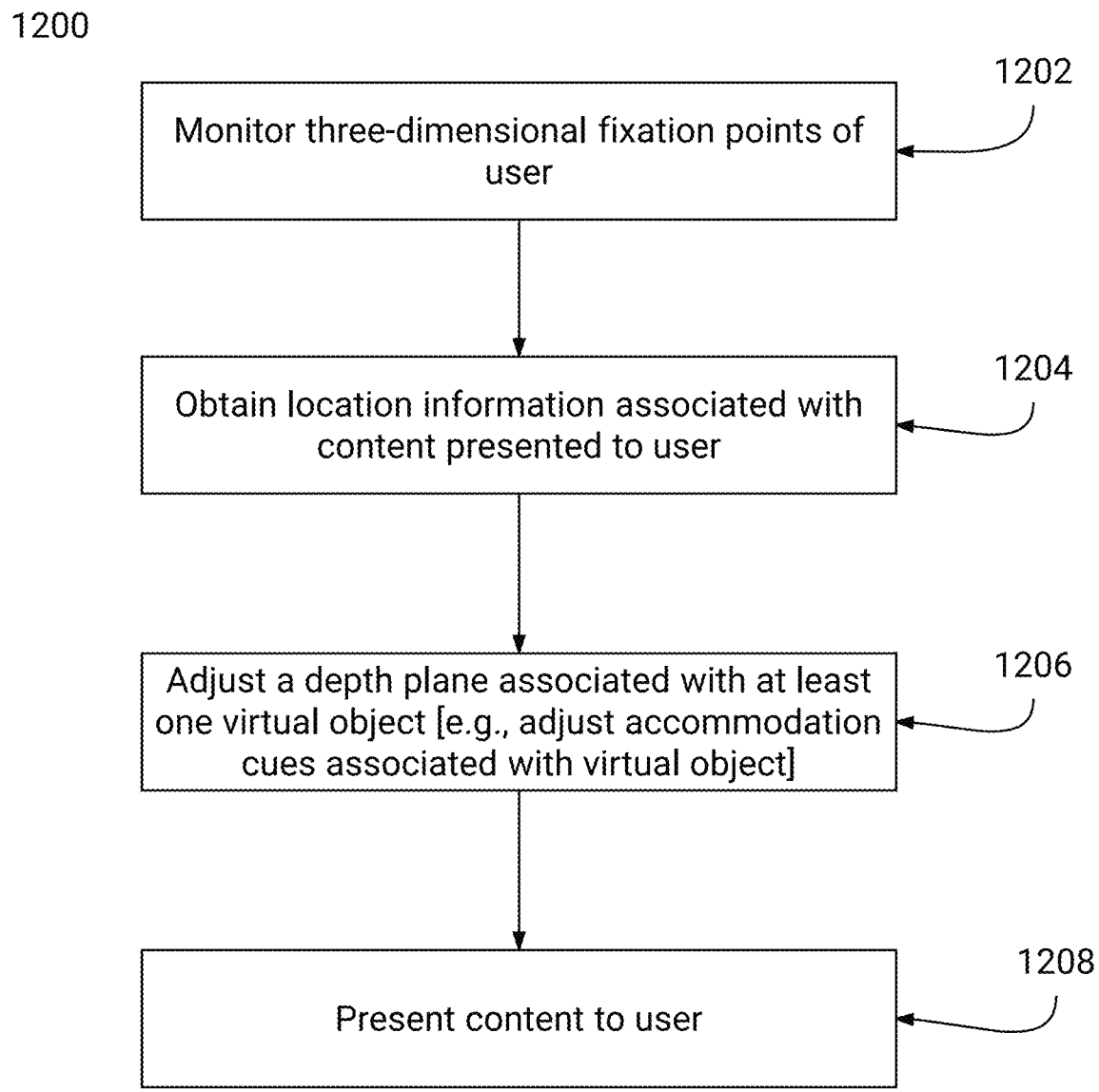
FIG. 12 illustrates a flowchart of an example process for adjusting a perceived depth plane associated with a virtual object.

FIG. 12 illustrates a flowchart of an example process 1200 for adjusting a depth plane associated with a virtual object. For convenience, the process 1200 may be described as being performed by a display system (e.g., the wearable display system 60, which may include processing hardware and software, and optionally may provide information to an outside system of one or more computers or other processing, for instance to offload processing to the outside system, and receive information from the outside system).

At block 1202, the display system monitors three-dimensional fixation points of a user's eyes. As described above, the display system may include sensors to monitor information associated with the user's eyes (e.g., the orientation of the eyes). A non-exhaustive list of sensors includes infrared sensors, ultraviolet sensors, and visible wavelength light sensors. The sensors may optionally output infrared, ultraviolet, visible light, and/or polarized light onto the user's eyes, and determine reflections of the outputted light from the user's eyes. As an example, infrared light may be output by an infrared light emitter, and an infrared light sensor. It will be appreciated that the sensor, which may include a light emitter, may correspond to the imaging device 630 of FIG. 6.

The display system may utilize the sensors to track the user's fixation by determine a gaze associated with each eye (e.g., a vector extending from the user's eye, such as extending from the fovea through the lens of the eye), and an intersection of the gazes of each eye. For example, the display system may output infrared light on the user's eyes, and reflections from the eye (e.g., corneal reflections) may be monitored. A vector between a pupil center of an eye (e.g., the display system may determine a centroid of the pupil, for instance through infrared imaging) and the reflections from the eye may be used to determine the gaze of the eye. The intersection of the gazes may therefore be assigned as the three-dimensional fixation point. Optionally, the display system may utilize orientation information associated with the display system (e.g., information describing an orientation of the display system in three-dimensional space) when determining the fixation point.

The display system may monitor determined fixation points to track objects that the user is viewing. For example, the display system may determine that the user is viewing a first virtual object based on a determined three-dimensional fixation point corresponding to a three-dimensional location at which the first virtual object is presented. Additionally, the display system may determine that the user is fixating at a location not corresponding to a virtual object, and may determine that a real-world object is likely located at the fixation point.

At block 1204 the display system obtains location information associated with virtual objects for presentation to the user. Prior to rendering the virtual objects for presentation to the user (e.g., via outputs of waveguides, as described above), the display system may obtain three-dimensional location information associated with the virtual objects. For instance, as described above, the virtual objects may be presented to the user such that the content appears to be located in the real-world (e.g., the content may be located at different depth planes within the user's field of view). It will be appreciated that the display system may include, or may have access to, a three-dimensional map of the ambient environment, including the intended locations of any virtual content in this ambient environment. With reference to this map, the display system may access and provide information specifying three-dimensional locations of virtual content within the user's field of view (e.g., locations within a display frustum, as illustrated in FIGS. 10A-10B).

As described above, location information for a virtual object may include a three-dimensional location. Based on the three-dimensional location, the virtual object may be associated with a particular depth plane (e.g., as illustrated and described in FIG. 11), such that if the user fixates on the virtual object, the particular depth plane may be utilized to present all virtual content for each frame until the user switches fixation.

At block 1206 the display system adjusts a depth plane associated with a virtual object. As described above, with respect to FIGS. 10A-10B, the display system may determine that the user is switching between two or more fixation points greater than a threshold metric, e.g., greater than a threshold number of times or greater than a threshold frequency. For example, the user may switch between a first fixation point and a second fixation point once every 30 seconds, every minute, every several minutes, and so on. If the first fixation point and second fixation point are associated with different depth planes, for example as illustrated in FIG. 11, if the fixation points are located in distinct depth plane volumes, then the display system could be required to present content for a different depth plane every time the user switches between the fixation points (e.g., without utilizing the techniques described herein).

The display system may therefore adjust a depth plane associated with a virtual object. As described herein, this may include associating the virtual object with a depth plane of another object (e.g., virtual object, real-world object) the user is also fixating on. That is, the accommodation cues associated with the virtual object (e.g., wavefront divergence) may be adjusted to correspond to a different depth plane. The display system may utilize the obtained location information to determine the virtual object's three-dimensional location, and may update the location information with the adjusted depth plane. As described above, the display system may select a virtual object to adjust according to a frequency with which the virtual object is being fixated upon. For example, if the user is fixating on a first virtual object greater than a second virtual object, the display system may adjust the second virtual object so that it is presented on the depth plane on which the first virtual object is already being presented.

Additionally, in some embodiments, the display system may obtain an indication of a virtual object that is to be adjusted. As an example, the user may indicate that a particular virtual object is to be given preference with respect to the adjustment, such that other virtual objects are adjusted and the particular virtual object remains at its associated depth plane. As another example, virtual objects that are moving (e.g., moving faster than a threshold rate) may be given preference, for example, to decrease distractions caused by an non-fixated object. Optionally the display system may obtain indications of virtual objects that are not to be adjusted. Furthermore, the display system may optionally obtain indications of virtual objects that are to remain linked and in focus to the user, such that they are presented at a same depth plane, no matter what adjustments are made. For example, the display system may present five virtual objects, and may ensure that two of the five virtual objects remain in focus (e.g., the two virtual objects may be presented at a same depth plane).

At block 1208 the display system presents the adjusted content to the user. For example, the adjusted virtual object may be output to the user with an adjusted wavefront divergence. That is, if the user fixates on the virtual object, the virtual object may be output to the user with a wavefront divergence corresponding to the adjusted depth plane, and not its original depth plane (as indicated by the display system's map of the ambient environment). An example of adjusting wavefront divergence is adjusting a particular waveguide from which the virtual object is to be displayed, where different waveguides output light with different amounts of wavefront divergence.

Figure 13:
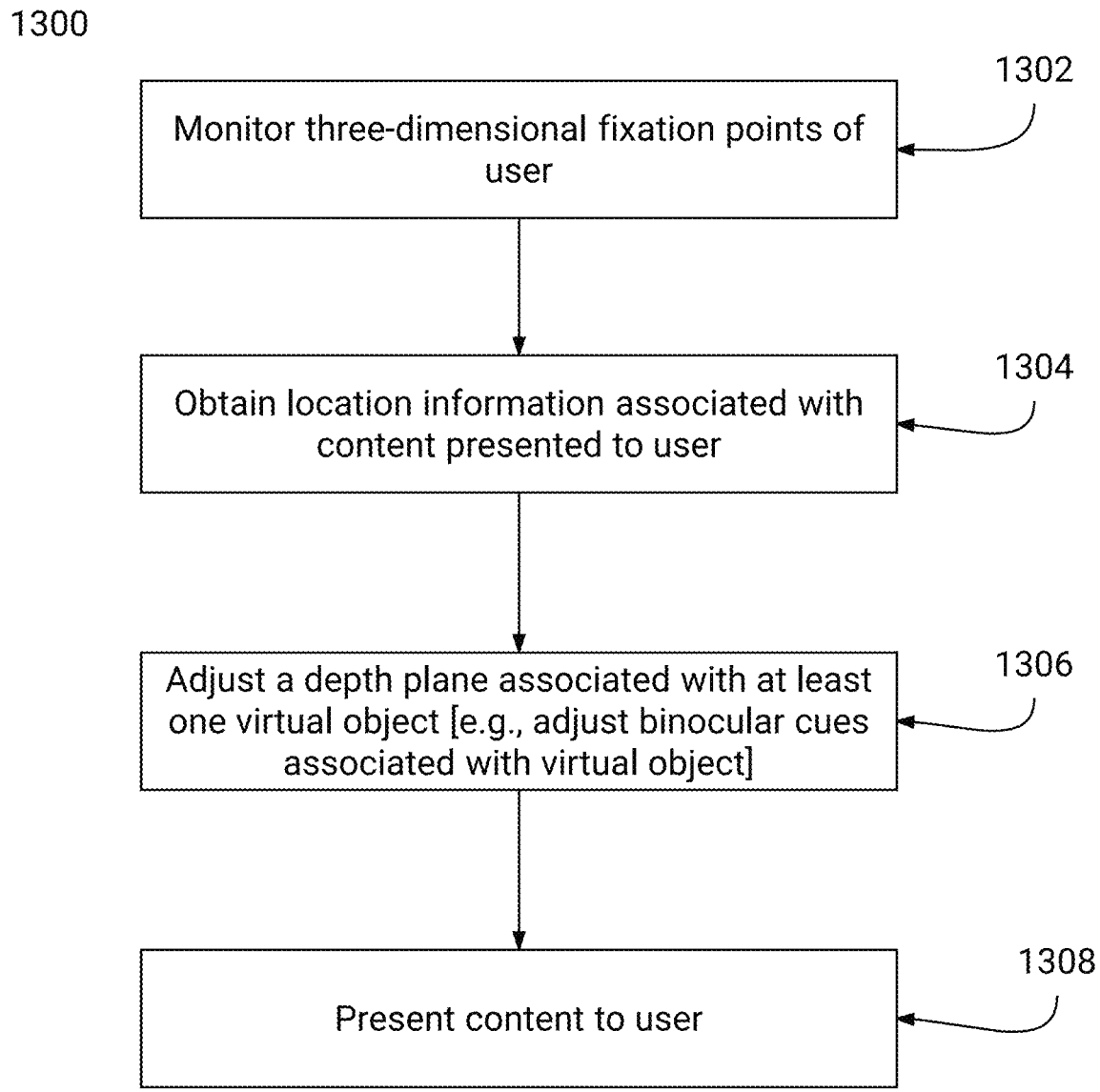
FIG. 13 illustrates a flowchart of another example process for adjusting a perceived depth plane associated with a virtual object.

FIG. 13 illustrates a flowchart of another example process 1300 for adjusting a depth plane associated with a virtual object. For convenience, the process 1300 may be described as being performed by a display system (e.g., the wearable display system 60, which may include processing hardware and software, and optionally may provide information to an outside system of one or more computers or other processing, for instance to offload processing to the outside system, and receive information from the outside system).

At block 1302 the display system monitors three-dimensional fixation points, and the display system obtains location information associated with presented content in block 1304, similar to blocks 1202, 1204, respectively (FIG. 12). At block 1306, the display system adjusts a depth plane associated with a virtual object. As described above, with respect to FIG. 12 (e.g., block 1206), the display system may associate the virtual object with a different depth plane, thereby adjusting accommodation cues associated with the virtual object. In contrast, at block 1306 the display system may adjust binocular cues to adjust a perceived depth of the virtual object. That is, the display system may adjust views of the virtual object that are provided to each eye of the user, such an adjustment may involve adjusting binocular disparity of the virtual content through dichoptic presentation. In this way, the virtual object can appear to be presented at a same, or similar, depth as other virtual content, or at a depth different from the virtual object's original depth. The display system then presents the adjusted content to the user at block 1308, as described above for block 1208 with respect to FIG. 12.

Figure 14:
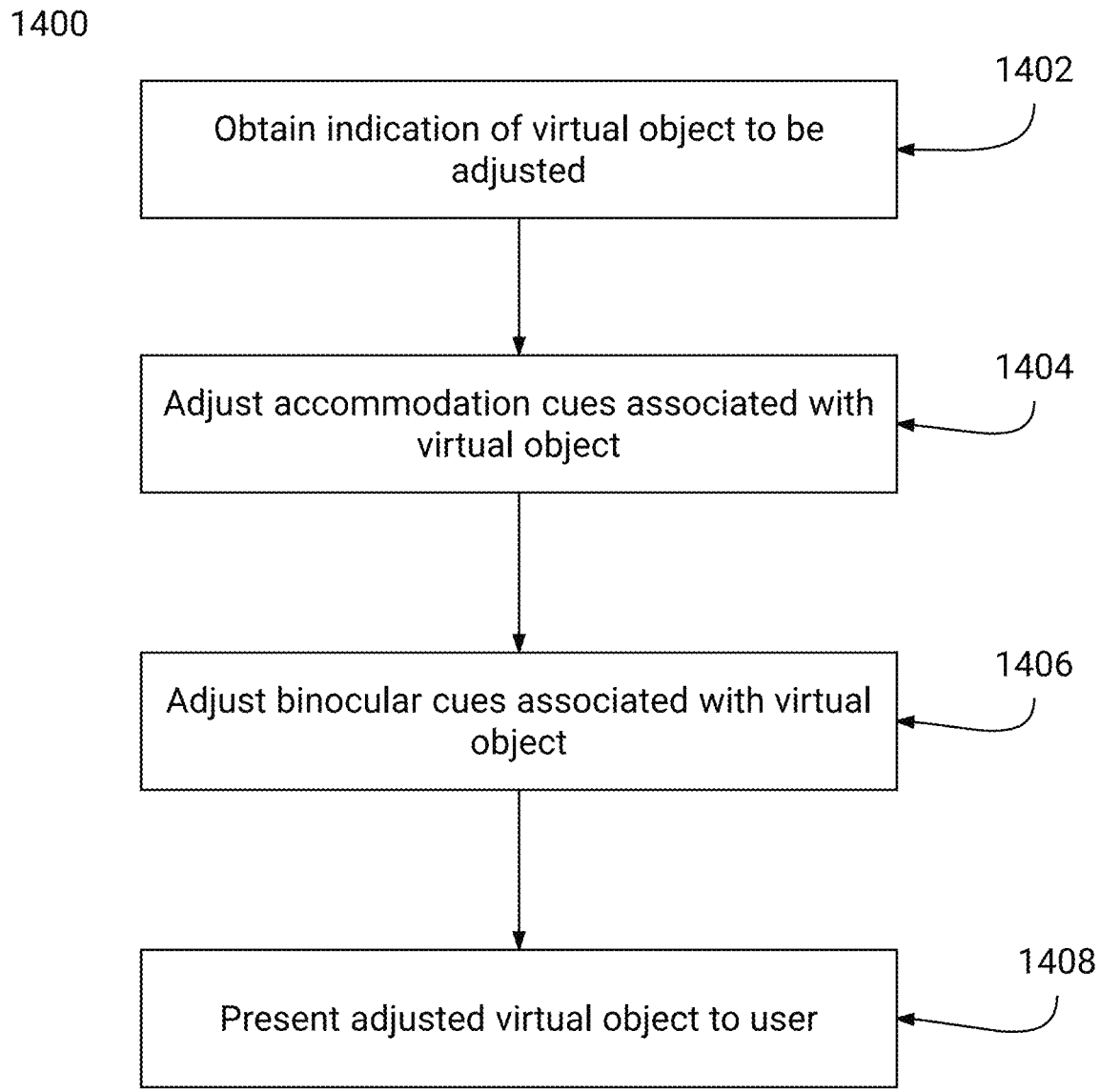
FIG. 14 illustrates a flowchart of an example process for adjusting accommodation cues and binocular cues associated with a virtual object.

FIG. 14 illustrates a flowchart of an example process for adjusting accommodation cues and binocular cues associated with a virtual object. For convenience, the process 1300 may be described as being performed by a display system (e.g., the wearable display system 60, which may include processing hardware and software, and optionally may provide information to an outside system of one or more computers or other processing, for instance to offload processing to the outside system, and receive information from the outside system).

At block 1402, the display system obtains an indication of a virtual object to be adjusted, as discussed above for blocks 1202, 1204 (FIG. 12). As described above, the presentation of a particular virtual object, or one or more virtual objects, may be adjusted with respect to an associated depth plane.

At block 1404, accommodation cues associated with the virtual object are adjusted. As described herein, a depth plane associated with the virtual object may be adjusted relative to the depth plane indicated by the display system's map. In some embodiments, the wavefront divergence of the virtual object may be adjusted so that it is the same as one or more other virtual objects on which the user is also fixating on. Since adjusting the depth plane adjusts wavefront divergence, by utilizing binocular disparity, the virtual object may be perceived by the user as being at a same, unadjusted, three-dimensional location. For example, the display system may present the same views of the virtual object to each eye of the user as would have been presented without adjusting the wavefront divergence of the virtual object, for example, by maintaining the same dichoptic presentations. Therefore even if a wavefront divergence of output light is adjusted, the user will perceive the virtual object at a same three-dimensional location in space (e.g., due to binocular disparity). As described above, adjusting the wavefront divergence and not binocular cues (e.g., the views of the virtual object provided to the user), may introduce a perceptible mismatch to the user.

Advantageously, in some embodiments, display system adjusts binocular cues associated with the virtual object at block 1406 so that those binocular cues are consistent with changes in the accommodation cues noted above. To reduce the mismatch between vergence and accommodation, for example, the display system may adjust the views of the virtual object that are presented to each eye of the user. For example, if the accommodation cues associated with the virtual object are adjusted such that depth is perceived to be closer to the user, the display system may similarly adjust the binocular cues to correspond to that closer depth. As described above with respect to FIGS. 10A-10B, the display system may implement an adjustment of the binocular cues after determining that the user is switching between two or more fixation points greater than a threshold metric, e.g., greater than a threshold number of times or greater than a threshold frequency.

At block 1408, the adjusted virtual content is presented to the user. Since both the accommodation cues and the binocular cues are being adjusted, the virtual content will be perceived as being located at a new location in three-dimensional space corresponding to the updated depth. Since the virtual content will be perceived at the new location, optionally the display system may update the location information associated with the virtual content to correspond to the new location.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Accordingly, the claims are not intended to be limited to the embodiments shown herein, but are to be accorded the widest scope consistent with this disclosure, the principles and the novel features disclosed herein.

What is claimed is:

1. A system comprising:
   a display device comprising a stack of waveguides, the stack of waveguides forming a display area and providing a view of an ambient environment through the display area, wherein a first waveguide of the stack of waveguides comprises diffractive optical elements configured to output light with a first wavefront divergence corresponding to a first accommodation cue and wherein a second waveguide of the stack of waveguides comprises diffractive optical elements configured to output light with a second wavefront divergence corresponding to a second accommodation cue;
   one or more processors configured to provide access to information from a map of the ambient environment, the map comprising respective three-dimensional locations for a first virtual object and a second virtual object, wherein a location for the first virtual object is associated with the first wavefront divergence and has associated binocular depth cues, and wherein the second virtual object is associated with the second wavefront divergence and second binocular depth cues; and
   one or more computer storage media storing instructions that, when executed by the one or more processors, cause the one or more processors to perform operations comprising:
   determining an indication of a fixation point of a user's eyes, wherein the fixation point corresponds to a location of the first virtual object;
   obtaining, via the map, location information associated with the second virtual object, wherein the second virtual object is configured to be presented, via the display device, with the second wavefront divergence from the second waveguide and with the second binocular depth cues;

subsequently changing the wavefront divergence associated with the second virtual object to correspond with the first wavefront divergence of the first virtual object, wherein the second binocular depth cues of the second virtual object are retained, wherein changing the wavefront divergence associated with the second virtual object causes an increase in an accommodation vergence mismatch of the second virtual object as long as the accommodation vergence mismatch of the second virtual object is below a threshold value, and wherein the subsequently changing the wavefront divergence includes adjusting the first accommodation cue based on an indication of a user input for other virtual objects to be adjusted to be at a same depth as the second virtual object, wherein the subsequently changing the wavefront divergence includes adjusting the first accommodation cue based on an indication of a user input for other virtual objects to be adjusted to be at a same depth as the second virtual object, the user input being independent of the determination of the fixation point of the user's eyes with respect to the first virtual object relative to the second virtual object, and wherein the user input includes at least one of a hand gesture, a voice input, an interaction with a totem, or a predetermined user preference; and causing presentation to the user, via the first waveguide of the display device, of the second virtual object with the adjusted second wavefront divergence, wherein, upon determining that the accommodation vergence mismatch exceeds the threshold value, the system is configured to change the second binocular depth cues to reduce the accommodation vergence mismatch to below the threshold value.

2. The system of claim 1,
wherein the subsequently changing the wavefront divergence includes adjusting the first accommodation cue further based on a determination that the first virtual object is being fixated on less than the second virtual object, and wherein determining the indication of the fixation point comprises determining that the user's eyes are fixating on the location for greater than a threshold duration.

3. The system of claim 1,
wherein the subsequently changing the wavefront divergence includes adjusting the first accommodation cue further based on a determination that the first virtual object is being fixated on less than the second virtual object, and wherein subsequently changing the wavefront divergence further comprises determining that the user is alternating fixation, at greater than a threshold frequency, between the first virtual object and the second virtual object.

4. The system of claim 1, wherein the accommodation-vergence mismatch threshold is 0.33 diopter.

5. The system of claim 1,
wherein the display device is a vari-focal display device, and wherein at least some waveguides of the plurality of waveguides are configured to output light of different component colors than other waveguides.

6. The system of claim 1, wherein the depth cues further comprise size cues.

7. A display system comprising:
a display device configured to present virtual objects to a user on a plurality of depth planes, wherein each depth plane has a different associated accommodation cue;
one or more processors; and
one or more computer storage media storing instructions that when executed by the display system, cause the display system to perform operations comprising:
accessing a map of the world that comprises respective locations for a first virtual object and a second virtual object, the first virtual object being presented on a first depth plane;
determining an indication of a fixation point of the eyes of the user, the fixation point corresponding to the location of the first virtual object, wherein the determining the indication of the fixation point includes a user input indication of a user input for other virtual objects to be adjusted to be at a same depth as the second virtual object;
the user input being independent of the determination of the fixation point of the user's eyes with respect to the first virtual object relative to the second virtual object, and
wherein the user input includes at least one of a hand gesture, a voice input, an interaction with a totem, or a predetermined user preference; and
based on the determined indication of the fixation point, changing display properties of the second virtual object such that the second virtual object is displayed on the first depth plane,
wherein the second virtual object was configured to be presented on a second depth plane of the plurality of depth planes based on the map, wherein display of the second virtual object is changed to the first depth plane, wherein displaying the second virtual object on the first depth plane causes an increase in an accommodation vergence mismatch of the second virtual object to a threshold value, and wherein the system is configured to change the second binocular depth cues based on a determination that the accommodation vergence mismatch exceeds the threshold value.

8. The display system of claim 7,
wherein the determining the indication of the fixation point further includes a determination that the first virtual object is being fixated on less than the second virtual object, and
wherein determining the indication of the fixation point comprises determining that the fixation point falls on the depth plane for greater than a threshold metric before changing display properties of the second virtual object.

9. The display system of claim 7,
wherein the determining the indication of the fixation point further includes a determination that the first virtual object is being fixated on less than the second virtual object, and
wherein changing display properties of the second virtual object comprises determining that the second virtual object is being fixated upon less than the first virtual object.

10. The display system of claim 7, wherein the accommodation-vergence mismatch threshold is 0.33 diopter.

11. The display system of claim 7, wherein the display device is a vari-focal display device.

12. A method comprising:
by a system comprising one or more processors and a display device comprising a stack of waveguides forming a display area and providing a view of an ambient environment through the display area, the display device configured to present virtual objects to a user on a plurality of depth planes, wherein each depth plane has a different associated accommodation cue:

accessing a map of the world that comprises respective positions for a first virtual object and a second virtual object, the first virtual object being presented via a first waveguide of the stack of waveguides, the first waveguide configured to output light with a first level of wavefront divergence, wherein the first virtual object has associated first binocular depth cues and the second virtual object has an associated second level of wavefront divergence and second binocular depth cues which are different from the first level of wavefront divergence and the first binocular depth cues;

determining an indication of a fixation point of a user's eyes, wherein the fixation point corresponds to a location of the first virtual object;

obtaining, via the map, location information associated with the second virtual object, wherein the second virtual object is configured to be presented, via the display device, with the second level of wavefront divergence and second binocular depth cues, and wherein a second waveguide of the stack of waveguides is configured to present virtual objects with the second accommodation cues;

subsequently changing the wavefront divergence associated with the second virtual object to correspond with the first level of wavefront divergence, wherein the second binocular cues of the second virtual object are retained, wherein changing the wavefront divergence associated with the second virtual object causes an increase in an accommodation vergence mismatch of the second virtual object to a threshold value, wherein the subsequently changing the wavefront divergence includes adjusting the first accommodation cue based on an indication of a user input for other virtual objects to be adjusted to be at a same depth as the second virtual object, wherein the subsequently changing the wavefront divergence includes adjusting the first accommodation cue based on an indication of a user input for other virtual objects to be adjusted to be at a same depth as the second virtual object, the user input being independent of the determination of the fixation point of the user's eyes with respect to the first virtual object relative to the second virtual object, and wherein the user input includes at least one of a hand gesture, a voice input, an interaction with a totem, or a predetermined user preference, wherein, upon a determination that the accommodation vergence mismatch exceeds the threshold value, changing the second binocular depth cues such that the second virtual object is perceived by the user to be in a common plane as the first virtual object; and causing presentation to the user, via the first waveguide of the display device, of the second virtual object with the first level of wavefront divergence and the second binocular depth cues.

13. The method of claim 12,
wherein the subsequently changing the wavefront divergence includes adjusting the first accommodation cue further based on a determination that the first virtual object is being fixated on less than the second virtual object, and
wherein determining the indication of the fixation point comprises determining that the user's eyes are fixating on the location for greater than a threshold duration.

14. The method of claim 12,
wherein the subsequently changing the wavefront divergence includes adjusting the first accommodation cue further based on a determination that the first virtual object is being fixated on less than the second virtual object, and
wherein subsequently changing the wavefront divergence comprises: determining that the user is alternating fixation, at greater than a threshold frequency, between the first virtual object and the second virtual.

15. The method of claim 12, wherein the display device is a vari-focal display device, and wherein at least some waveguides of the stack of waveguides are configured to output light with different component colors than other waveguide.

16. The system of claim 1,
wherein the subsequently changing the wavefront divergence includes adjusting the first accommodation cue further based on a determination that the first virtual object is being fixated on less than the second virtual object, and
wherein the subsequently changing the wavefront divergence includes the determination that the first virtual object is being fixated on less than the second virtual object.

17. The system of claim 1, wherein the changing the second binocular depth cues upon determining that the accommodation vergence mismatch exceeds the threshold value includes changing the second binocular depth cues such that the second virtual object is perceived by the user to be in a common plane as the first virtual object.

18. The system of claim 1, wherein the changing the second binocular depth cues upon determining that the accommodation vergence mismatch exceeds the threshold value includes changing the second binocular depth cues such that the second virtual object is perceived by the user to be closer to the user but in a different plane than the first virtual object.

* * * * *